US011254626B2

(12) United States Patent
Weinberger et al.

(10) Patent No.: US 11,254,626 B2
(45) Date of Patent: Feb. 22, 2022

(54) PROCESS FOR SEPARATING HYDROCARBON COMPOUNDS

(71) Applicant: Lummus Technology LLC, The Woodlands, TX (US)

(72) Inventors: Sam Weinberger, San Francisco, CA (US); Justin Dwight Edwards, League City, TX (US); Julian Wolfenbarger, Landenberg, PA (US); Srinivas R. Vuddagiri, Davis, CA (US); Iraj Isaac Rahmim, San Francisco, CA (US)

(73) Assignee: Lummus Technology LLC, The Woodlands, TX (US)

( * ) Notice: Subject to any disclaimer, the term of this patent is extended or adjusted under 35 U.S.C. 154(b) by 12 days.

(21) Appl. No.: 16/287,006

(22) Filed: Feb. 27, 2019

(65) Prior Publication Data
US 2020/0031736 A1 Jan. 30, 2020

Related U.S. Application Data

(63) Continuation of application No. 15/354,886, filed on Nov. 17, 2016, now abandoned, which is a
(Continued)

(51) Int. Cl.
*B01J 8/02* (2006.01)
*F25J 3/02* (2006.01)
(Continued)

(52) U.S. Cl.
CPC .............. *C07C 2/84* (2013.01); *B01J 8/0005* (2013.01); *B01J 8/02* (2013.01); *C10G 27/04* (2013.01);
(Continued)

(58) Field of Classification Search
None
See application file for complete search history.

(56) References Cited

U.S. PATENT DOCUMENTS 2,324,172 A 7/1943 Parkhurst
2,486,980 A 11/1949 Robinson
(Continued)

FOREIGN PATENT DOCUMENTS

CA 2041874 C 4/1999
CA 2765769 A1 1/2011
(Continued)

OTHER PUBLICATIONS

Agarwal, et al., Aqueous Au—Pd colloids catalyze selective CH4 oxidation to CH3OH with O2 under mild conditions, Science 358, Oct. 13, 2017, 223-27.
(Continued)

*Primary Examiner* — Jennifer A Leung
(74) *Attorney, Agent, or Firm* — Calfee, Halter & Griswold LLP

(57) ABSTRACT

Disclosed herein are processes for producing and separating ethane and ethylene. In some embodiments, an oxidative coupling of methane (OCM) product gas comprising ethane and ethylene is introduced to a separation unit comprising two separators. Within the separation unit, the OCM product gas is separated to provide a $C_2$-rich effluent, a methane-rich effluent, and a nitrogen-rich effluent. Advantageously, in some embodiments the separation is achieved with little or no external refrigeration requirement.

10 Claims, 8 Drawing Sheets

Related U.S. Application Data continuation of application No. 14/820,460, filed on Aug. 6, 2015, now Pat. No. 9,527,784, which is a continuation of application No. 13/739,954, filed on Jan. 11, 2013, now Pat. No. 9,133,079.

(60) Provisional application No. 61/586,711, filed on Jan. 13, 2012.

(51) Int. Cl.

| | | |
|---|---|---|
| *C07C 2/84* | (2006.01) | |
| *C10G 27/04* | (2006.01) | |
| *C10G 29/20* | (2006.01) | |
| *C10G 31/06* | (2006.01) | |
| *B01J 8/00* | (2006.01) | |

(52) U.S. Cl.
CPC ........... *C10G 29/205* (2013.01); *C10G 31/06* (2013.01); *F25J 3/0219* (2013.01); *F25J 3/0233* (2013.01); *F25J 3/0238* (2013.01); *F25J 3/0242* (2013.01); *F25J 3/0257* (2013.01); *B01J 2208/00256* (2013.01); *B01J 2208/026* (2013.01); *F25J 2205/04* (2013.01); *F25J 2210/12* (2013.01); *F25J 2215/62* (2013.01); *F25J 2220/02* (2013.01); *F25J 2230/30* (2013.01); *F25J 2235/60* (2013.01); *F25J 2240/02* (2013.01); *F25J 2245/02* (2013.01)

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,516,262 A * | 6/1970 | Bernstein ............... F25J 3/0233 62/619 |
| 3,584,071 A | 6/1971 | McNulty et al. |
| 3,596,473 A | 8/1971 | Streich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,115,086 A * | 9/1978 | Jordan ............... F25J 3/0242 62/622 |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,418,045 A * | 11/1983 | Sato ............... B01D 53/864 423/245.3 |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,519,824 A * | 5/1985 | Huebel ............... C07C 7/09 62/621 |
| 4,523,049 A | 6/1985 | Jones et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,889,545 A * | 12/1989 | Campbell ............... C07C 7/04 62/621 |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,113,032 A * | 5/1992 | Cameron ............... C07C 2/84 585/500 |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |

(56) References Cited

U.S. PATENT DOCUMENTS

| | | |
|---|---|---|
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,245,099 A | 9/1993 | Mitariten |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,457,256 A | 10/1995 | Mitariten et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Koster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,602,920 B2 | 8/2003 | Hall et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |

(56) References Cited

U.S. PATENT DOCUMENTS

| | | | |
|---|---|---|---|
| 7,793,517 B2* | 9/2010 | Patel | F25J 3/0209 62/617 |
| 7,795,490 B2 | 9/2010 | Iaccino et al. | |
| 7,799,209 B2 | 9/2010 | Petri | |
| 7,799,730 B2 | 9/2010 | Ringer et al. | |
| 7,838,710 B2 | 11/2010 | Ryu | |
| 7,868,216 B2 | 1/2011 | Chodorge et al. | |
| 7,879,119 B2 | 2/2011 | Abughazaleh et al. | |
| 7,888,541 B2 | 2/2011 | Gartside et al. | |
| 7,888,543 B2 | 2/2011 | Iaccino et al. | |
| 7,902,113 B2 | 3/2011 | Zarrinpashne et al. | |
| 7,915,461 B2 | 3/2011 | Gattis et al. | |
| 7,915,462 B2 | 3/2011 | Gattis et al. | |
| 7,915,463 B2 | 3/2011 | Gattis et al. | |
| 7,915,464 B2 | 3/2011 | Gattis et al. | |
| 7,915,465 B2 | 3/2011 | Gattis et al. | |
| 7,915,466 B2 | 3/2011 | Gattis et al. | |
| 7,932,296 B2 | 4/2011 | Malhotra et al. | |
| 7,968,020 B2 | 6/2011 | Behelfer et al. | |
| 7,968,759 B2 | 6/2011 | Iaccino et al. | |
| 7,977,519 B2 | 7/2011 | Iaccino et al. | |
| 7,993,500 B2 | 8/2011 | Gilliam et al. | |
| 7,993,599 B2 | 8/2011 | Leveson | |
| 8,021,620 B2 | 9/2011 | Nicholas et al. | |
| 8,071,836 B2 | 12/2011 | Butler | |
| 8,080,215 B2 | 12/2011 | Taheri et al. | |
| 8,119,848 B2 | 2/2012 | Cross, Jr. et al. | |
| 8,129,305 B2 | 3/2012 | Bagherzadeh et al. | |
| 8,137,444 B2 | 3/2012 | Farsad et al. | |
| 8,153,851 B2 | 4/2012 | Gartside et al. | |
| 8,163,070 B2 | 4/2012 | Hees et al. | |
| 8,192,709 B2 | 6/2012 | Reyes et al. | |
| 8,227,650 B2 | 7/2012 | Putman et al. | |
| 8,232,415 B2 | 7/2012 | Taheri et al. | |
| 8,258,358 B2 | 9/2012 | Gartside et al. | |
| 8,269,055 B2 | 9/2012 | Fritz et al. | |
| 8,277,525 B2 | 10/2012 | Dalton | |
| 8,293,805 B2 | 10/2012 | Khan et al. | |
| 8,399,527 B1 | 3/2013 | Brown et al. | |
| 8,399,726 B2 | 3/2013 | Chinta et al. | |
| 8,404,189 B2 | 3/2013 | Andresen et al. | |
| 8,435,920 B2 | 5/2013 | White et al. | |
| 8,450,546 B2 | 5/2013 | Chinta et al. | |
| 8,524,625 B2 | 9/2013 | Dight et al. | |
| 8,552,236 B2 | 10/2013 | Iaccino | |
| 8,557,728 B2 | 10/2013 | Birdsall et al. | |
| 8,575,410 B2 | 11/2013 | Nicholas et al. | |
| 8,624,042 B2 | 1/2014 | Grasset et al. | |
| 8,658,750 B2 | 2/2014 | Lattner et al. | |
| 8,669,171 B2 | 3/2014 | Perraud et al. | |
| 8,710,286 B2 | 4/2014 | Butler | |
| 8,729,328 B2 | 5/2014 | Chinta et al. | |
| 8,742,189 B2 | 6/2014 | Kiesslich et al. | |
| 8,742,192 B2 | 6/2014 | Godsmark et al. | |
| 8,748,681 B2 | 6/2014 | Nicholas et al. | |
| 8,748,682 B2 | 6/2014 | Nicholas et al. | |
| 8,759,598 B2 | 6/2014 | Hayashi et al. | |
| 8,765,660 B1 | 7/2014 | Li et al. | |
| 8,796,497 B2 | 8/2014 | Chinta et al. | |
| 8,865,780 B2 | 10/2014 | Bogild Hansen | |
| 8,912,109 B2 | 12/2014 | Chinta et al. | |
| 8,912,381 B2 | 12/2014 | Chinta et al. | |
| 8,921,256 B2 | 12/2014 | Cizeron et al. | |
| 8,962,517 B2 | 2/2015 | Zurcher et al. | |
| 8,993,473 B2 | 3/2015 | Melde et al. | |
| 9,040,762 B2 | 5/2015 | Cizeron et al. | |
| 9,079,815 B2 | 7/2015 | Mukherjee et al. | |
| 9,133,079 B2 | 9/2015 | Weinberger et al. | |
| 9,321,702 B2 | 4/2016 | Nyce et al. | |
| 9,321,703 B2 | 4/2016 | Nyce et al. | |
| 9,328,297 B1 | 5/2016 | Nyce et al. | |
| 9,334,204 B1 | 5/2016 | Radaelli et al. | |
| 9,352,295 B2 | 5/2016 | Rafique et al. | |
| 9,371,257 B2 | 6/2016 | Chinta et al. | |
| 9,376,324 B2 | 6/2016 | Senderov et al. | |
| 9,446,343 B2 | 9/2016 | Elliott et al. | |
| 9,446,397 B2 | 9/2016 | Gamoras et al. | |
| 9,469,577 B2 | 10/2016 | Schammel et al. | |
| 9,512,047 B2 | 12/2016 | Nyce et al. | |
| 9,527,784 B2 | 12/2016 | Weinberger et al. | |
| 9,556,086 B2 | 1/2017 | Schammel et al. | |
| 9,567,269 B2 | 2/2017 | Radaelli et al. | |
| 9,598,328 B2 | 3/2017 | Nyce et al. | |
| 9,670,113 B2 | 6/2017 | Iyer et al. | |
| 9,682,900 B2 | 6/2017 | Keusenkothen et al. | |
| 9,701,597 B2 | 7/2017 | Rafique et al. | |
| 9,718,054 B2 | 8/2017 | Scher et al. | |
| 9,738,571 B2 | 8/2017 | Schammel et al. | |
| 9,751,079 B2 | 9/2017 | Freer et al. | |
| 9,751,818 B2 | 9/2017 | Zurcher et al. | |
| 9,790,144 B2 | 10/2017 | Radaelli et al. | |
| 9,944,573 B2 | 4/2018 | Radaelli et al. | |
| 9,950,971 B2 | 4/2018 | Henao et al. | |
| 9,956,544 B2 | 5/2018 | Schammel et al. | |
| 9,969,660 B2 | 5/2018 | Iyer et al. | |
| 9,975,767 B2 | 5/2018 | Farnell | |
| 10,047,020 B2 | 8/2018 | Cizeron et al. | |
| 10,195,603 B2 | 2/2019 | Scher et al. | |
| 10,300,465 B2 | 5/2019 | Freer et al. | |
| 10,301,234 B2 | 5/2019 | Nyce et al. | |
| 10,308,565 B2 | 6/2019 | Schammel et al. | |
| 10,377,682 B2 | 8/2019 | Ratique et al. | |
| 10,407,361 B2 | 9/2019 | Radaelli et al. | |
| 10,787,398 B2 | 9/2020 | Nyce et al. | |
| 10,787,400 B2 | 9/2020 | Radaelli et al. | |
| 10,793,490 B2 | 10/2020 | Radaelli et al. | |
| 2002/0007101 A1 | 1/2002 | Senetar et al. | |
| 2002/0015670 A1 | 2/2002 | Shah et al. | |
| 2002/0150522 A1 | 10/2002 | Heim et al. | |
| 2002/0182735 A1 | 12/2002 | Kibby et al. | |
| 2003/0033932 A1 | 2/2003 | Sirkar et al. | |
| 2003/0045761 A1 | 3/2003 | Kuechler et al. | |
| 2003/0072700 A1 | 4/2003 | Goebel et al. | |
| 2003/0094398 A1 | 5/2003 | Porter et al. | |
| 2003/0189202 A1 | 10/2003 | Li et al. | |
| 2003/0233019 A1 | 12/2003 | Sherwood | |
| 2004/0158113 A1 | 8/2004 | Srinivas et al. | |
| 2004/0220053 A1 | 11/2004 | Bagherzadeh et al. | |
| 2004/0231586 A1 | 11/2004 | Dugue et al. | |
| 2004/0242940 A1 | 12/2004 | Takahashi et al. | |
| 2005/0065391 A1 | 3/2005 | Gattis et al. | |
| 2005/0065392 A1 | 3/2005 | Peterson et al. | |
| 2005/0107650 A1 | 5/2005 | Sumner | |
| 2005/0154228 A1 | 7/2005 | Nakajima et al. | |
| 2005/0239634 A1 | 10/2005 | Ying et al. | |
| 2006/0018821 A1 | 1/2006 | Suzuki et al. | |
| 2006/0021379 A1* | 2/2006 | Ronczy | F25J 3/0238 62/620 |
| 2006/0063955 A1 | 3/2006 | Lacombe et al. | |
| 2006/0155157 A1 | 7/2006 | Zarrinpashne et al. | |
| 2006/0194995 A1 | 8/2006 | Umansky et al. | |
| 2006/0235246 A1 | 10/2006 | Smith et al. | |
| 2006/0283780 A1 | 12/2006 | Spivey et al. | |
| 2007/0027030 A1 | 2/2007 | Cheung et al. | |
| 2007/0073083 A1 | 3/2007 | Sunley | |
| 2007/0083073 A1 | 4/2007 | Bagherzadeh et al. | |
| 2007/0112236 A1 | 5/2007 | Bridges et al. | |
| 2007/0135668 A1 | 6/2007 | Sumner | |
| 2007/0244347 A1 | 10/2007 | Ying et al. | |
| 2008/0121383 A1 | 5/2008 | Birk | |
| 2008/0138274 A1 | 6/2008 | Garcia-Martinez | |
| 2008/0141713 A1 | 6/2008 | Verma | |
| 2008/0154078 A1 | 6/2008 | Bozzano et al. | |
| 2008/0194900 A1 | 8/2008 | Bhirud | |
| 2008/0207975 A1 | 8/2008 | Crone et al. | |
| 2008/0267852 A1 | 10/2008 | Schumacher et al. | |
| 2008/0275143 A1 | 11/2008 | Malhotra et al. | |
| 2008/0281136 A1 | 11/2008 | Bagherzadeh et al. | |
| 2008/0293980 A1 | 11/2008 | Kiesslich et al. | |
| 2008/0300436 A1 | 12/2008 | Cheung et al. | |
| 2009/0005236 A1 | 1/2009 | Ying et al. | |
| 2009/0042998 A1 | 2/2009 | Hashimoto et al. | |
| 2009/0043141 A1 | 2/2009 | Mazanec et al. | |
| 2009/0087496 A1 | 4/2009 | Katusic et al. | |

(56) References Cited

U.S. PATENT DOCUMENTS

| | | |
|---|---|---|
| 2009/0105066 A1 | 4/2009 | Kang et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0140144 A1 | 6/2010 | Clinton et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0256245 A1 | 10/2010 | Iaccino et al. |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2012/0302807 A1 | 11/2012 | Elseviers |
| 2013/0023079 A1 | 1/2013 | Kang et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0246856 A1 | 9/2015 | Schmigalle et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0057889 A1 | 3/2017 | Sarsani et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0062642 A1 | 2/2019 | Wei et al. |
| 2019/0119182 A1 | 4/2019 | McCormick et al. |

(56) References Cited

U.S. PATENT DOCUMENTS

| | | |
|---|---|---|
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0048165 A1 | 2/2020 | Duggal et al. |
| 2020/0055796 A1 | 2/2020 | Nyce et al. |
| 2020/0071242 A1 | 3/2020 | Patel et al. |
| 2020/0172452 A1 | 6/2020 | Duggal et al. |
| 2020/0189994 A1 | 6/2020 | Radaelli et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 608447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 133336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A2 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |

OTHER PUBLICATIONS

Ahari, et al. Effects of operating parameters on oxidative coupling of methane over Na—WMn/SiO2 catalyst at elevated pressures. Journal of Natural Gas Chemistry. vol. 20, Issue 2, Mar. 2011, pp. 204-213.

American Petroleum Institute Publication 534 Heat Recovery Steam Generators Jan. 1995 (51 pages).

Autothermal Partial Oxidative Coupling of Methane. IP.com, Prior Art Database Technical Disclosure, Jul. 29, 2008, 5 pages.

Barrett, et al. The determination of pore volume and area distributions in porous substances—Compuatations from nitrogen isotherms. J. Am. Chem. Soc., 1951, vol. 73, pp. 373-380.

Berstad, D. et al. Low-temperature CO2 removal from natural gas. Energy Procedia (2012) 26:41-48.

Bloch, et al. Hydrocarbon Separations in a Metal-Organic Framework with Open Iron(II) Coordination Sites, Science, 2012, 335:1606-1610.

Bollmann, et al. Ethylene tetramerization: a new route to produce 1-octene in exceptionally high selectivities. J Am Chem Soc. Nov. 17, 2004;126(45):14712-3.

Botella, et al. Effect of Potassium Doping on the Catalytic Behavior of Mo—V—b Mixed Oxide Catalysts in the oxidation of Propane to Acrylic Acid. Catalysis Letters, Sep. 2003, vol. 89, Issue 3-4, pp. 249-253.

Carter, et al. High activity ethylene trimerisation catalysts based on diphosphine ligands. Chem Commun (Camb). Apr. 21, 2002;(8):858-9.

Caskey, et al., Dramatic Tuning of Carbon Dioxide Uptake via Metal Substitution in a Coordination Polymer with Cylindrical Pores, J. Am. Chem. Soc., (2009), 130(33): 10870-71.

Cavani, et al. Oxidative dehydrogenation of ethane and propane: How far from commercial implementation? Catalysis Today. 2007; 127(1-4):113-131.

(56) References Cited

OTHER PUBLICATIONS

Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted Lal 03 Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Labinger. Oxidative coupling of methane: an inherent limit to selectivity? Catal. Lett. 1988; 1:371-376.
Forma, From Microporous to Mesoporous Molecular Sieve Materials and Their Use in Catalysis, Chern. Rev., 97, 1997, pp. 2373-2419.
Debart, et al. α-MNO2 Nanowires: A catalyst for the 02 Electrode in Rechargeabl Lithium Batteries. Angewandte Chemie International Edition 47: 4521-4524, 2008.
Dietzel, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Li, B. et al. Advances in CO2 capture technology: A patent review. Applied Energy (2013) 102:1439-1447.
Enger, et al. A review of catalytic partial oxidation of methane to synthesis gas with emphasis on reaction mechanisms over transition metal catalysts. Applied Catalysis A: General 346 (1-2): 1-27, Aug. 2008.
Fallah, et al., A New Nano-(2Li20/Mg0) Catalyst/Porous Alpha-Alumina Composite for the Oxidative Coupling of Methane Reaction, AlChE Journal, Mar. 2010, 56(3):717-28.
Gao, et al. A study on methanol steam reforming to CO2 and H2 over the La2 C04 nanofiber catalyst. Journal of Solid State Chemistry 181: 7-13, 2008.
Gao, et al. The direct decomposition of NO over the La2 Cu04 nanofiber catalyst. Journal of Solid State Chemistry 181: 2804-2807, 2008.
Geier, et al., Selective adsorption of ethylene over ethane and propylene over propane in the metal-organic frameworks M2(dobdc) (M=Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v.106 pp. 684-694.
Goto et al, Mesoporous Material from Zeolite, Journal of Poruous Materials, 2002, pp. 43-48.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of The Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4(4):128-131.

Haag, W.O. et al. Aromatics, Light Olefins and Gasoline from Methanol: Mechanistic Pathways with ZSM-5 Zeolite Catalyst. J Mol Catalysis (1982) 17:161-169.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.
Huang, et al. Exploiting shape effects of La2O3 nanocrystals for oxidative coupling of methane reaction. Nanoscale 5 (22): 10844-10848, 2013.
Huang, et al. Exploiting shape effects of La2O3 nanocrystals for oxidative coupling of methane reaction. Nanoscale—Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Li, et al. Combined Single-Pass Conversion of Methane Via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core Au shell Nanowires and Their Surface Enhanced Raman Spectroscopic Studies. Acta Chimica Sinica. 65 (9): 779-784, 2007.
Liu, et al. A novel Na2 W04-Mn.SiC monolithic foam catalyst with improved thermal properties for the oxidativec coupling of methane. Catalysis Communications 9: 1302-1306, 2008.
Liu, et al. Increasing the Density of Adsorbed Hydrogen with Coordinatively Unsaturated Metal Centers in Metal-Organic Frameworks Langmuir, 2008, 24:4772-77.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Mokhatab et al. "Handbook of Natural Gas Transmission and Processing: Principles and Practices" 2015. Chapter 1, pp. 237-242. (Year: 2015).
Morgan, C.R. et al. Gasoline from Alcohols. Ind Eng Chem Prod Res Dev(1981) 20:185-190.

(56) References Cited

OTHER PUBLICATIONS

Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of $La_2O_3CO_3$ nanowires with high surface areas. Jounral of the Chinese Rare Earth Society 23 (Spec. Issue): 33-36, Dec. 2005.
Nyce, et al. PCT/US2015/010525 filed Jan. 7, 2015 for Ethylene-to-Liquids Systems and Methods.
Ogura et al. Formation of Uniform Mesopores in ZSM-5 Zeolite through Treatment in Alkaline Solution, Chemistry Letters, 2000, pp. 882-883.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over $Mn/NA_2WO_4/SiO_2$ and $MN/NA_2WO_4/MgO$ Catalysts. Journal of Catalysis 179:222-230, 1998.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Process Systems; "Steam Tables" Apr. 8, 201—https://web.archive.org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK—Conference, Hamburg, Germany (2007).
Sheridan, D. et al. PCT/US2014/067465 filed Nov. 25, 2014 for Integrated Mixers and Heat Exchangers for Oxidative Coupling Methane Systems.
Simons, K. Membrane Technologies for CO2 Capture. Dissertation, U. of Twente (2010).
Smith, et al. Recent developments in solvent absorption technologies at the CO2CRC in Australia. Energy Procedia 1 (2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Tabak, S.A. et al. Conversion of Methanol over ZSM-5 to Fuels and Chemicals. Cat Today (1990) 307-327.
Takanabe, et al. Mechanistic Aspects and Reaction Pathways for Oxidative Coupling of Methane on $Mn/NA_2WO_4/SiO_2$ Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by $Mn/NA_2WO_4/SiO_2$. Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Wang, et al. Autothermal oxidative coupling of methane on the $SrCO_3/Sm_2O_3$ catalysts. Catalysis communications 10: 807-810, 2009.
Wang, et al. Comparative study on oxidation of methane to ethane and ethylene over $NA_2WO_4-Mn/SiO_2$ catalysts prepared by different methods_ Journal of Molecular Catalysis A: Chemical 245:272-277, 2006.
Duan, et al. Three-dimensional copper (II) metal-organic framework with open metal sites and anthracene nucleus for highly selective $C_2H_2/CH_4$ and $C_2NH_2/CO_2$ gas separation at room temperature. Microporous and Mesoporous Materials. vol. 181, Nov. 15, 2013, pp. 99-104.
He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.
Chemical Engineering—"Separation Processes: Supercritical CO2: A Green Solvent" Feb. 1, 2010.
Wang, et al. Low temperature selective oxidation of methane to ethane and ethylene over $BaCO_3/La_2O_3$ catalysts prepared by urea combustion method. Catalysis communications 7: 5963, 2006.
Wang, et al., Critical Influence of $BaCO_3$ on Low Temperature Catalytic Activity of $BaCO_3/ZrO_2$ Catalysts for Oxidative Coupling of Methane, Catalysis Letters (2009), 129:156-162.
Water Electrolysis & Renewable Energy Systems. FuelCellToday (May 2013).
Wikipedia search, Adiabatic Process, Mar. 2011, 10 pages.
Witek-Krowiak, A. et al. Carbon Dioxide Removal in a Membrane Contactor-Selection of Absorptive Liquid/Membrane System. Intl J Chem Eng and Appl. (2012) 3(6):391-395.
Wong, et al. Oxidative coupling of methane over alkali metal oxide promoted $LaO_3/BaCO_3$ catalysts. J. Chem. Tech. Biotechnol. 65:351-354, 1996.
Wu, et al., High-Capacity Methane Storage in Metal-Organic Frameworks M2(dhtp): The Important Role of Open Metal Sites, J. Am. Chem. Soc. 131 (13):4995-5000.
Xu, et al. Maximise ethylene gain and acetylene selective hydrogenation efficiency. Petroleum technology quarterly 18.3 (2013): 39-42.
Xu, G. et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires. Nanotechnology 17: 2304-2310, 2006.
Yu, et al. Oxidative coupling of methane over acceptor-doped $SrTiO_3$: Correlation between p-type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement): 285-289, 2004.

(56) References Cited

OTHER PUBLICATIONS

Zhou, et al. Functionalization of lanthanum hydroxide nanowires by atom transfer radical polymerization. Nanotechnology 18, 2007, 7 pages.
Zhou. BP-UOP Cyclar Process. Handbook of Petroleum Refining Processes, The McGraw-Hill Companies (2004), pp. 2.29-2.38.
Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
International search report and written opinion dated Mar. 17, 2014 for PCT Application No. PCT/US2013/021312.
Office action dated Oct. 23, 2014 for U.S. Appl. No. 13/739,954.
Notice of allowance dated Jun. 8, 2015 for U.S. Appl. No. 13/739,954.
Office action dated May 20, 2016 for U.S. Appl. No. 14/820,460.
Notice of allowance dated Aug. 22, 2016 for U.S. Appl. No. 14/820,460.
Office Action dated Jan. 25, 2018 for U.S. Appl. No. 15/354,886.
U.S. Appl. No. 15/354,886 Office Action dated Aug. 31, 2018.
Notice of Acceptance dated Jun. 28, 2017 for AU Application No. 2013207783.
Office Action dated Jul. 30, 2018 for CA Application No. 2,860,773.
Notice of Allowance dated May 8, 2020 for CA Application No. 2,860,773.
Examination Report dated Dec. 8, 2016 for AU Application No. 2013207783.

\* cited by examiner

PROCESS FOR SEPARATING HYDROCARBON COMPOUNDS

CROSS REFERENCE

This application is a continuation of U.S. patent application Ser. No. 15/354,886, filed Nov. 17, 2016, which is a continuation of U.S. patent application Ser. No. 14/820,460, filed Aug. 6, 2015, now U.S. Pat. No. 9,527,784, which is a continuation of U.S. patent application Ser. No. 13/739,954, filed Jan. 11, 2013, now U.S. Pat. No. 9,133,079, which claims the benefit of U.S. Provisional Patent Application Ser. No. 61/586,711, filed Jan. 13, 2012, each of which is incorporated herein by reference in its entirety.

BACKGROUND

Technical Field

This disclosure generally relates to selectively separating carbon compounds containing at least two carbon atoms from a mixed gas stream provided by a chemical process.

Description of the Related Art

The modern petrochemical industry makes extensive use of cracking and fractionation technology to produce and separate various desirable compounds from crude oil. Cracking and fractionation operations are energy intensive and generate considerable quantities of greenhouse gases. The gradual depletion of worldwide petroleum reserves and the commensurate increase in petroleum prices places extraordinary pressure on refiners to minimize losses and improve efficiency when producing products from existing feedstocks, and also to seek viable alternative feedstocks capable of providing affordable hydrocarbon intermediates and liquid fuels to downstream consumers.

Methane provides an attractive alternative feedstock for the production of hydrocarbon intermediates and liquid fuels due to its widespread availability and relatively low cost when compared to crude oil. Worldwide methane reserves are estimated in the hundreds of years at current consumption rates and new production stimulation technologies promise to make formerly unattractive methane deposits commercially viable.

Used in the production of polyethylene plastics, polyvinyl chloride, ethylene oxide, ethylene chloride, ethylbenzene, alpha-olefins, linear alcohols, vinyl acetate, and fuel blendstocks such as but not limited to aromatics, alkanes, alkenes, ethylene is one of the most important commodity chemical intermediates currently produced. With economic growth in developed and developing portions of the world, demand for ethylene and ethylene based derivatives continues to increase. Currently, ethylene production is limited to high volume production as a commodity chemical in a relatively large steam cracker or other petrochemical complex setting due to the high cost of the crude oil feedstock and the large number of hydrocarbon byproducts generated in the crude oil cracking process. Producing ethylene from far more abundant and significantly less expensive natural gas provides an attractive alternative to ethylene derived from crude oil. Oligomerization processes can be used to further convert ethylene into longer chain hydrocarbons such as $C_6$ and $C_8$ hydrocarbons useful for polymer gasoline and high value specialty chemicals.

The conversion of methane to longer chain hydrocarbons, particularly alkenes such as ethylene, produces a product gas containing multiple byproducts, unreacted feedstock gases, and inert components in addition to ethylene. The ability to selectively and economically produce and separate methane based alkenes on a commercially viable scale provides a pathway to a significant new source of ethylene useful for production of ethylene based derivatives.

BRIEF SUMMARY

As noted above, the present disclosure is directed to methods for providing $C_2$ carbon compounds via oxidative coupling of methane (OCM). The methods may be summarized as including steps of:

a) combining a feedstock gas comprising methane with an oxygen containing gas comprising oxygen;

(b) contacting the combined feedstock gas and oxygen containing gas with a catalyst and providing an OCM product gas comprising ethane and ethylene ($C_2$);

(c) compressing the OCM product gas;

(d) condensing at least a portion of the OCM product gas to provide an OCM product gas condensate comprising mostly water;

(e) introducing the OCM product gas condensate to a first separator;

(f) isentropically expanding and reducing the temperature of a first portion of the OCM product gas;

(g) introducing the first portion of the OCM product gas to the first separator and introducing a second portion of the OCM product gas to a second separator, the second separator operating at a lower pressure and temperature than the first separator;

(h) removing a $C_2$-rich effluent and a methane/nitrogen containing gas mixture from the first separator;

(i) introducing the methane/nitrogen containing gas mixture to the second separator; and (j) removing a methane-rich effluent and a nitrogen-rich effluent from the second separator.

In certain embodiments of the disclosed methods, the oxygen containing gas is compressed air having an oxygen content of about 21 mol % and a nitrogen content of about 78 mol %; and the nitrogen content in the methane/nitrogen containing gas removed from the first separator may be at least about 85 mol %. In yet other embodiments, the first and second separators may operate at a below ambient temperature; and adiabatic expansion of at least one of the OCM product gas, a methane gas, a nitrogen gas, or a methane/nitrogen gas mixture may provide at least a portion of the cooling to produce the below ambient temperature. In other embodiments, the oxygen containing gas is compressed oxygen having an oxygen content of at least about 90 mol % and a nitrogen content of at most about 10 mol %; and the nitrogen content in the methane/nitrogen containing gas removed from the first separator may be at most about 85 mol %. In yet other embodiments, the first and second separators may operate at a below ambient temperature; and the compressed oxygen may be supplied via a cryogenic process and the cryogenic process may provide at least a portion of the cooling to produce the below ambient temperature.

Methods for providing $C_2$ carbon compounds via oxidative coupling of methane (OCM) in accordance with embodiments described herein may further include introducing at least a portion of the methane-rich effluent removed from the second separator to the feedstock gas prior to combining the feedstock gas with the oxygen containing gas. In certain embodiments, the $C_2$-rich effluent may include at least about 90.0 mol % $C_2$, the methane-rich effluent may include at least about 92.0 mol % methane, and the nitrogen-rich effluent may include at least about 85.0 mol % nitrogen.

In other embodiments disclosed herein, methods for providing $C_2$ carbon compounds via oxidative coupling of methane (OCM) may further include reducing water content in the OCM product gas to about 0.001 mol % at most prior to condensing at least a portion of the OCM product gas.

Methods for providing $C_2$ carbon compounds via oxidative coupling of methane (OCM) in accordance with disclosed embodiments may further include reducing carbon dioxide content in the OCM product gas to about 5 ppm at most prior to condensing at least a portion of the OCM product gas.

Other embodiments of methods for providing $C_2$ carbon compounds via oxidative coupling of methane (OCM) may further include reducing hydrogen sulfide content in the feedstock gas to about 5 ppm. In certain embodiments disclosed herein, the feedstock gas may include at least about 20 mol % methane and compressing the OCM product gas may include increasing the pressure of the OCM product gas to at least about 100 pounds per square inch gauge (psig).

In another aspect of the disclosed subject matter processes for separating $C_2$ compounds from a product of an oxidative coupling of methane (OCM) process may be summarized as including:

(a) providing an OCM product gas from an OCM process, the OCM product gas comprising ethane and ethylene;

(b) compressing the OCM product gas to a pressure of at least about 200 pounds per square inch gauge (psig);

(c) reducing the temperature of the OCM product gas and condensing at least a portion of the OCM product gas to provide an OCM product gas condensate;

(d) separating the OCM product gas condensate from the OCM product gas;

(e) introducing the OCM product gas condensate to a first separator;

(f) separating the OCM product gas separated from the OCM product gas condensate into a first portion and a second portion and isentropically expanding the first portion of the OCM product gas through a turboexpander to reduce the temperature of the first portion of the OCM product gas;

(g) introducing the first portion of the OCM product gas to the first separator;

(h) removing a $C_2$-rich effluent from the first separator;

(i) removing a first separator overhead gas from the first separator;

(j) reducing the temperature of the first separator overhead gas;

(k) introducing the cooled first separator overhead gas to a second separator;

(l) removing a methane-rich effluent from the second separator; and (m) removing a nitrogen-rich effluent from the second separator.

In additional embodiments of the present disclosure, methods for separating $C_2$ compounds from a product of an oxidative coupling of methane (OCM) process may further include:

(n) reducing the temperature of the second portion of the OCM product gas;

(o) adiabatically expanding the second portion of the OCM product gas to provide an at least partially condensed mixed stream that includes a second OCM product gas condensate and a second OCM product gas;

(p) introducing the at least partially flashed second OCM product gas condensate to the first separator; and (q) reducing the temperature of the second OCM product gas and introducing the second OCM product gas to the second separator.

Methods for separating $C_2$ compounds from a product of an oxidative coupling of methane (OCM) process in accordance with disclosed embodiments of this aspect of the present disclosure may further include reducing water concentration in the OCM product gas to about 0.001 mole percent (mol %) at most and more preferably to about 0.0001 mol % (1 ppmv) at most prior to condensing at least a portion of the OCM product gas.

In other embodiments, methods for separating $C_2$ compounds from a product of an oxidative coupling of methane (OCM) process may further include reducing carbon dioxide concentration in the OCM product gas to about 10 ppmv at most prior to condensing at least a portion of the OCM product gas.

In other embodiments, methods for separating $C_2$ compounds from a product of an oxidative coupling of methane (OCM) process may further include reducing acetylene concentration in the OCM product gas to about 1 part per million by volume (ppmv) at most prior to condensing at least a portion of the OCM product gas or reducing the acetylene concentration in a $C_2$-rich effluent provided by the separations unit to about 1 ppmv at most.

In accordance with other disclosed embodiments of this aspect of the present disclosure, methods for separating $C_2$ compounds from a product of an oxidative coupling of methane (OCM) process may further include reducing hydrogen sulfide concentration in the OCM process to about 5 ppm at most using sulfur removal process, system and/or device, such as a sulfur trap. In other embodiments, providing the OCM product gas may include combining compressed air comprising oxygen and nitrogen and having an oxygen concentration of at least about 21 mol % with a feedstock gas comprising methane and having a methane concentration of at least 50 mol % and introducing the combined compressed air and feedstock gas to at least one OCM reactor. In other embodiments, the OCM product gas may include about 90 mol % or less nitrogen and providing the OCM product gas may include combining an oxygen containing gas comprising compressed oxygen and having an oxygen concentration of at least about 90 mol % with a feedstock gas comprising methane and having a methane concentration of at least about 50 mol % and introducing the combined compressed oxygen and feedstock gas to at least one OCM reactor. In certain embodiments, the OCM product gas may include about 10 mol % or less nitrogen.

In yet other embodiments, the method for separating $C_2$ compounds from a product of an oxidative coupling of methane (OCM) process disclosed herein may further include recycling at least a portion of the methane-rich effluent from the second separator to an OCM reactor. In other embodiments, the $C_2$-rich effluent may include at least about 90 mol % $C_2$, the methane-rich effluent may include at least about 60 mol % methane, and the nitrogen-rich effluent may include at least about 50 mol % nitrogen.

In yet another aspect of the disclosed subject matter, processes for separating $C_2$ compounds from a product of an oxidative coupling of methane (OCM) process may be summarized as including:

(a) combining a feedstock gas comprising methane with an oxygen containing gas;

(b) contacting the combined feedstock gas and oxygen containing gas with a catalyst and providing an OCM product gas having a $C_2$ concentration of from about 0.5 mol % to about 20 mol %, a methane content of about 60 mole percent (mol %) or less, and a nitrogen content of at least about 20 mol %;

(c) compressing the OCM product gas; and separating the OCM product gas into a $C_2$-rich effluent; a methane-rich effluent; and an nitrogen-rich effluent.

In accordance with embodiments of this aspect of the disclosed subject matter, separating the OCM product gas into the $C_2$-rich effluent; the methane-rich effluent; and the nitrogen-rich effluent may occur at a lower than ambient temperature. In addition, in accordance with disclosed embodiments, adiabatic expansion of at least one of the OCM product gas, a methane gas, a nitrogen gas, or a methane/nitrogen gas mixture may provide at least a portion of the cooling to achieve the lower than ambient temperature and in other embodiments of the disclosed subject matter, adiabatic expansion of at least one of the OCM product gas, a methane gas, a nitrogen gas, or a methane/nitrogen gas mixture may provide all of the cooling to achieve the lower than ambient temperature.

In other embodiments, processes for separating $C_2$ compounds from a product of an oxidative coupling of methane (OCM) process may further include recycling at least a portion of the methane-rich effluent and combining it with the feedstock gas and/or the oxygen containing gas. In other embodiments, the $C_2$+ rich effluent may include at least about 90 mol % $C_2$+ compounds, the methane-rich effluent may include at least about 60 mol % methane, and the nitrogen-rich effluent may include at least about 50 mol % nitrogen. In other embodiments, compressing the OCM product gas may include increasing the pressure of the OCM product gas to at least about 200 pounds per square inch gauge (psig).

In another aspect of the disclosed subject matter, processes for separating ethylene from a product of an oxidative coupling of methane (OCM) process may be summarized as including:

(a) reducing the hydrogen sulfide content of a feedstock gas comprising methane to about 5 ppm at most;

(b) combining the feedstock gas with an oxygen containing gas comprising oxygen;

(c) passing the combined feedstock gas and oxygen containing gas across a catalyst to provide an OCM product gas having an ethylene content of about 0.5 mol % or greater, a hydrogen content of from about 0.0 mol % to about 4.0 mol %, a methane content of about 95 mol % or less, and a nitrogen content of at least about 1 mol %;

(d) compressing the OCM product gas; and (e) separating the OCM product gas into a ethylene-rich effluent; a methane-rich effluent; and an nitrogen-rich effluent.

In accordance with embodiments of this aspect of the disclosed subject matter, the OCM product gas exiting the OCM reactor may be at a temperature of no more than about 1750° F. (950° C.) or preferably no more than about 1650° F. (900° C.) and/or at a pressure of no more than 200 psig (690 kPa). In accordance with other embodiments, the catalyst may include a compound including at least one of an alkali metal, an alkaline earth metal, a transition metal, and a rare-earth metal.

In accordance with other embodiments, separating the OCM product gas into an ethylene-rich effluent; a methane-rich effluent; and a nitrogen-rich effluent may include:

(f) reducing the temperature of the OCM product gas and condensing at least a portion of the OCM product gas to provide an OCM product gas condensate;

(g) separating the OCM product gas condensate from the OCM product gas;

(h) introducing the OCM product gas condensate to a first separator;

(i) separating the OCM product gas separated from the OCM product gas condensate into a first portion and a second portion and isentropically expanding the first portion of the OCM product gas through a turboexpander to reduce the temperature of the first portion of the OCM product gas;

(j) introducing the first portion of the OCM product gas to the first separator;

(k) removing the ethylene-rich effluent from the first separator;

(l) removing a first separator overhead gas from the first separator;

(m) reducing the temperature of the first separator overhead gas;

(n) introducing the cooled first separator overhead gas to a second separator;

(o) removing the methane-rich effluent from the second separator; and (p) removing the nitrogen-rich effluent from the second separator.

In accordance with other embodiments of this aspect of the present disclosure, processes for separating ethylene from a product of an oxidative coupling of methane (OCM) process may further include recycling at least a portion of the methane-rich effluent from the second separator to the reduced hydrogen sulfide content feedstock gas. In other embodiments, the nitrogen-rich effluent may include about 50 mole percent (mol %) or greater nitrogen concentration, the methane-rich effluent may include about 60 mol % or greater methane concentration, and the ethylene-rich effluent may include from about 10 mol % to about 60 mol % or greater ethylene concentration. In additional embodiments, separating the OCM product gas into the ethylene-rich effluent; the methane-rich effluent; and the nitrogen-rich effluent may occur at a lower than ambient temperature and adiabatic expansion of at least one of the OCM product gas, a methane gas, a nitrogen gas, or a methane/nitrogen gas mixture may provide at least a portion of the cooling to provide the lower than ambient temperature.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
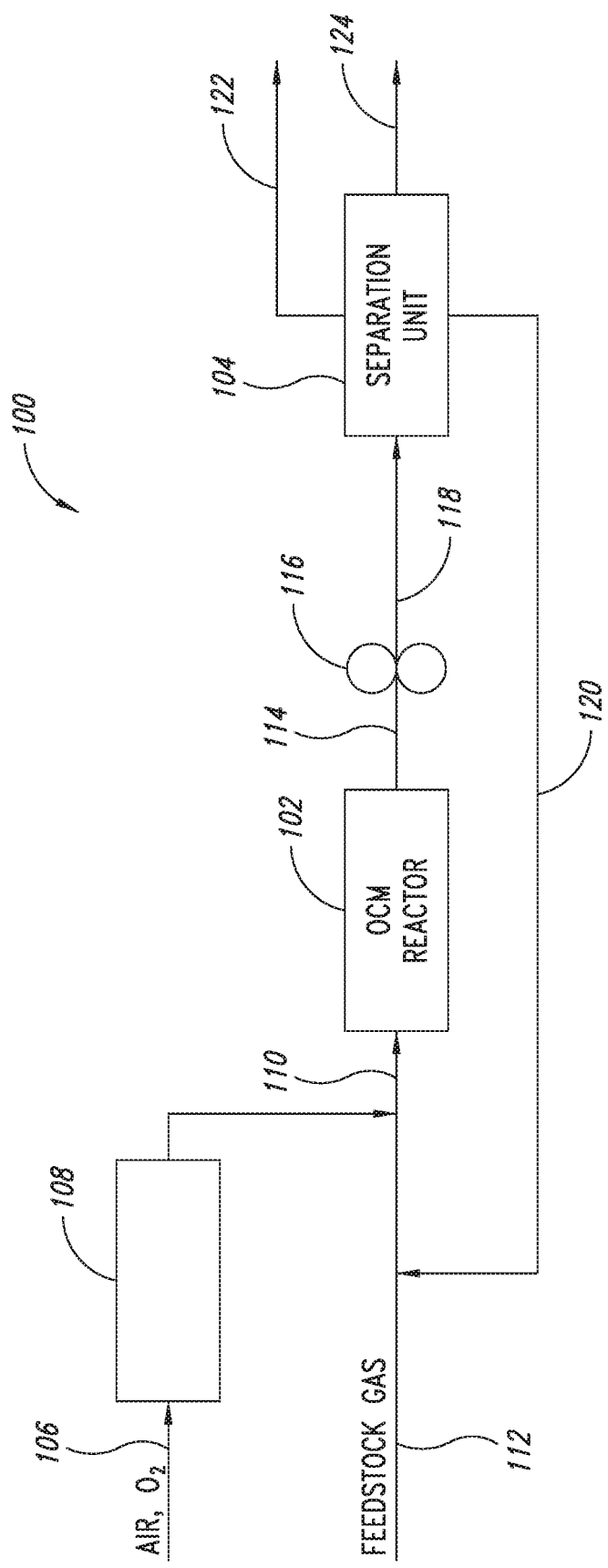
FIG. 1 is a block flow diagram depicting a methane based $C_2$ production and separation process, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with specific unit operations, such as fluid transport, heat transfer, mass transfer, thermodynamic processes, and mechanical processes, e.g., fluid transportation, filtration, evaporation, condensation, gas absorption, distillation, extraction, adsorption, drying, gas liquefaction, and refrigeration have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used in the specification and the appended claims, references are made to a "feedstock gas." It is understood that a feedstock gas may include any gas or gasified liquid containing methane and recognizable by one of ordinary skill in the art as being suitable for providing methane to a oxidative coupling of methane (OCM) reaction. As used in the specification and the appended claims, references are made to an "effluent." It is understood that an effluent may include any material or compound either removed or intended for removal from a particular location. Additionally, references are made to compositions that are variously described as being "nitrogen-rich," "methane-rich," and "$C_2$-rich." It should also be understood that the use of the suffix "-rich" indicates the compound or compounds having the greatest molar concentration within the composition. For example, a "nitrogen-rich effluent" describes an effluent where nitrogen has the greatest molar concentration. Similarly a "methane-rich gas" describes a gas where methane has the greatest molar concentration. As used in the specification and the appended claims, references are made to a "unit." It is understood that a unit may include any number of individual or combined unit operations such as separation, heating, cooling, condensation, vaporization, and the like as recognizable by one of ordinary skill in the art as being suitable or beneficial for achieving the indicated results. For example a "separation unit" may have more than one physical separator and may also include multiple ancillary heating, cooling, condensation and vaporization unit operations to achieve the desired separation.

As used herein the terms "$C_2$" and "$C_2$ compounds" refer to alkane (i.e., ethane) and alkene (i.e., ethylene) hydrocarbons and not to alkyne (i.e., acetylene) hydrocarbons comprising 2 carbon atoms in their backbone. C2+ refer to 2 chain length hydrocarbons and higher hydrocarbon chain length comprising both alkanes and alkenes, e.g. propane and propylene. As used herein the term "$C_2$ content" refers to the concentration of $C_2$ compounds (i.e., ethane+ethylene) present at the specified location.

The headings and Abstract of the Disclosure provided herein are for convenience only and do not interpret the scope or meaning of the appended claims or disclosed embodiments.

FIG. 1 is a block flow diagram depicting an illustrative $C_2$ production and separation process 100 including one or more oxidative coupling of methane (OCM) reactors 102 and one or more separation units 104. In process 100, the pressure of an oxygen containing gas 106 is increased, for example using one or more compressors 108, and the resultant higher pressure oxygen containing gas is combined with a feedstock gas 112 containing methane to provide a feedstock gas/oxygen containing gas mixture 110. The feedstock gas/oxygen containing gas mixture 110 is introduced to the one or more OCM reactors 102. Within the one or more OCM reactors 102, methane present in the feedstock gas and the oxygen present in the oxygen containing gas are passed over a catalyst promoting the formation of an OCM product gas 114 including ethylene and ethane. The OCM product gas 114 may also contain amounts of unreacted feedstock such as methane; inert compounds such as nitrogen; and byproducts such as hydrogen, water vapor, and various carbon oxides ($CO_x$).

In the embodiment of FIG. 1, the pressure of the OCM product gas 114 is increased, for example using one or more compressors 116 prior to introduction to the one or more separation units 104. Within the one or more separation units 104, at least three effluents are produced: a methane-rich effluent 120, a nitrogen rich effluent 122, and a $C_2$-rich effluent 124. At least a portion of the methane-rich effluent 120 may be recycled to the feedstock gas 112 or alternatively the methane-rich effluent 120 may not be recycled to the feedstock gas 112. Recycling of methane-rich effluent 120 is beneficial since methane is the feedstock for the production of $C_2$s, however recycling at least a portion of the methane-rich effluent 120 provides additional operational and economic benefits because the methane-rich effluent 120 can be utilized without having to meet the stringent requirements of a fungible product, for example a maximum nitrogen limit imposed on methane intended for injection into a natural gas transport or distribution systems.

The $C_2$-rich effluent 124 contains the desired ethane and ethylene compounds as well as $C_3$ and heavier hydrocarbon compounds such as propane and propylene (i.e., $C_{3+}$ compounds). In some instances the $C_2$ compounds, particularly the ethylene, present in the $C_2$-rich effluent 124 can be separated, for example using a $C_2$ splitter to selectively separate ethylene from ethane, and marketed as a commodity chemical. In other instances, all or a portion of the ethylene can be introduced to one or more additional unit operations, for example an oligomerization process to create oligomers, such as $C_6$ (trimer) and $C_8$ (tetramer) compounds, useful for example in liquid fuel products.

The oxygen containing gas 106 can include any source of oxygen such as air, purified oxygen, or mixtures thereof. The oxygen containing gas 106 can be an enriched oxygen containing gas sourced partially or wholly from an air separation plant or an air separation unit. The pressure of the oxygen containing gas 106 may be increased, for example using one or more compressors 108, to provide the higher pressure oxygen containing gas. In some embodiments, the temperature of the higher pressure oxygen containing gas can be adjusted, for example through the use of an intercooler and/or aftercooler installed and operated in conjunction with the one or more compressors 108. The addition of stoichiometric quantities of oxygen to the one or more OCM reactors via the oxygen containing gas 106 can limit the formation of undesirable combustion byproducts such as $CO_x$ within the one or more OCM reactors 102. In some instances, the temperature of the oxygen containing gas 106 may be increased, for example by thermally contacting the oxygen containing gas 106 with one or more higher temperature gases or liquids, prior to mixing with the feedstock gas 112.

The composition of the oxygen containing gas 106 can vary dependent upon the source of the gas. For example, where air is used to provide the oxygen containing gas, an oxygen content of about 21 mol % and a nitrogen content of about 78 mol % is provided. In at least some implementations, one or more inert gases, such as nitrogen, argon, or helium may be present in trace or larger quantities in the oxygen containing gas 106. Where purified oxygen is used to provide the oxygen containing gas, an oxygen content of greater than about 21 mol % is possible. The oxygen content of the oxygen containing gas 106 can be about 21 mol % or greater; about 40 mol % or greater; about 60 mol % or greater; or about 80 mol % or greater. Similarly, the nitrogen content of the oxygen containing gas 106 will vary dependent upon the source providing the oxygen containing gas 106. The nitrogen content of the oxygen containing gas can be about 78 mol % or less; about 60 mol % or less; about 40 mol % or less; or about 20 mol % or less. In at least some implementations, the nitrogen content of the oxygen containing gas can be from about 5 mole percent (mol %) to about 95 mol %; about 10 mol % to about 90 mol %; about 15 mol % to about 85 mol %; about 20 mol % to about 80 mol %; or about 25 mol % to about 75 mol %. The pressure of the compressed oxygen containing gas 110 can vary. For example, the pressure of the compressed oxygen containing gas can be about 300 psig (2100 kPa) or less; about 200 psig (1400 kPa) or less; or more preferably about 100 psig (700 kPa) or less.

The feedstock gas 112 includes methane, all or a portion of which may include methane from relatively clean sources such as that available from a pipeline, commercial or industrial supply or distribution network. In some instances, all or a portion of the feedstock gas 112 may be sourced from so called "dirty" sources such as extracted natural gas that contains contaminants or impurities requiring removal prior to introducing the feedstock gas 112 to the one or more OCM reactors 102. While in general, the use of a feedstock gas 112 having a known, fixed methane composition is preferred, gases having a variable methane composition may also be used to provide all or a portion of the feedstock gas 112. Similarly, while the use of a feedstock gas 112 having a high methane content is preferred, gases having low methane content may also be used to provide all or a portion of the feedstock gas 112 provided any components detrimental to catalyst life, catalyst performance, or any components promoting undesirable side reactions or the formation of undesirable products are partially or completely removed prior to introducing the feedstock gas 112 to the one or more OCM reactors 102. The methane content of the feedstock gas 112 can vary and be about 20 mol % or less, about 35 mol % or less, about 50 mol % or less, about 80 mol % or less; about 90 mol % or less; about 95 mol % or less; or about 99 mol % or less.

Contaminants present in the feedstock gas 112 can include heavier weight hydrocarbons, acid gases such as carbon dioxide and hydrogen sulfide, nitrogen, water vapor, natural gas condensate ("casinghead gasoline"), and mercury to name a few. The feedstock gas 112 can be pretreated using known techniques prior to introduction to the one or more OCM reactors 102 to remove some or all of the contaminants such as hydrogen sulfide and heavier weight hydrocarbons that are capable of promoting the formation of undesired reaction side- or by-products, and/or detrimentally affecting the performance of the OCM catalyst disposed within the one or more OCM reactors 102. After treatment, the hydrogen sulfide content of the feedstock gas 112 can be about 20 ppm or less; about 10 ppm or less; about 5 ppm or less; or about 1 ppm or less. After treatment the heavier weight hydrocarbons content of the feedstock gas 112 can be about 0.1 mol % or less; about 0.05 mol % or less; or about 0.01 mol % or less. Since the one or more OCM reactors 102 operate at an elevated temperature, the temperature of the feedstock gas 112 may be increased prior to mixing with the oxygen containing gas 106 to lessen the thermal input required to raise the temperature of the feedstock gas/oxygen containing gas mixture to the desired reaction temperature within the one or more OCM reactors 102.

In at least some embodiments the temperature and/or pressure of the feedstock gas 112 can be adjusted prior to mixing with the oxygen containing gas 106 or introduction to the one or more OCM reactors 102. The pressure and temperature of the feedstock gas 106 can vary. For example the pressure of the feedstock gas 112 can be about 150 psig (1035 kPa) or less; about 100 psig (690 kPa) or less; about 75 psig (520 kPa) or less; about 50 psig (345 kPa) or less; or about 30 psig (205 kPa) or less and the temperature of the feedstock gas 112 can be about 200° F. (93° C.) or less; about 150° F. (66° C.) or less; about 100° F. (38° C.) or about 30° F. (0° C.) or less.

The higher pressure oxygen containing gas may be introduced, mixed, or otherwise combined with the feedstock gas 112 either within the one or more OCM reactors 102 or prior to the entry of either, or both, the higher pressure oxygen containing gas and/or the feedstock gas 112 to the one or more OCM reactors 102. The feedstock gas/oxygen containing gas mixture 110 can be treated to remove one or more contaminants prior to introduction to the one or more OCM reactors 102. Contaminants present in the feedstock gas 112 may be detrimental to the OCM catalyst and/or the one or more OCM reactors 102 themselves and therefore the concentration of these contaminants is reduced prior to introducing the feedstock gas/oxygen containing gas mixture 110 to the one or more OCM reactors 102. For example, elemental sulfur or hydrogen sulfide may be present in concentrations ranging from trace amounts to double-digit mol % quantities within feedstock gas sources, such as extracted natural gas. The presence of sulfur or hydrogen sulfide can promote the formation of corrosive sulfurous acid within the one or more OCM reactors 102 and therefore are most desirably removed from the feedstock gas 112, oxygen containing gas 106 or the feedstock gas/oxygen containing gas mixture 110 prior to introducing the mixture to the one or more OCM reactors 102. After removal of sulfur or hydrogen sulfide, the hydrogen sulfide content of the feedstock gas/oxygen containing gas mixture 110 can be about 20 ppm or less; about 10 ppm or less; about 5 ppm or less; or more preferably about 1 ppm or less.

Additionally, the temperature of the feedstock gas/oxygen containing gas mixture 110 may be adjusted prior to introducing the mixture to the one or more OCM reactors 102. The temperature can be adjusted to a desired level to optimize the generation of preferred products such as ethylene within the one or more OCM reactors 102. In some instances, the temperature of the feedstock gas/oxygen containing gas mixture 110 may be adjusted in conjunction with one or more pretreatment steps, for example desulfurization of the feedstock gas/oxygen containing gas mixture 110. Prior to entering the one or more OCM reactors 102, the temperature of the feedstock gas/oxygen containing gas mixture 110 can be about 1300° F. (700° C.) or less; about 1110° F. (600° C.) or less; about 930° F. (500° C.) or less; about 750° F. (400° C.) or less; about 570° F. (300° C.) or less; or about 400° F. (200° C.) or less.

The OCM reactor 102 can include any vessel, device, system or structure capable of converting at least a portion of the feedstock gas/oxygen containing gas mixture 110 into one or more $C_2$ compounds using an oxidative coupling of methane process. The one or more OCM reactors 102 can be one or more similar or dissimilar reactors or reactor types arranged in series or parallel processing trains. The OCM process may be carried out in different types of commercially available reactors including a fixed bed reactor where the combined methane/oxygen gas mixture is passed through a structured bed; a fluidized bed reactor where the combined methane/oxygen mixture is used to fluidize a solid catalyst bed; and a membrane type reactor where the combined methane/oxygen mixture passes through an inorganic catalytic membrane.

The OCM reaction ($2CH_4+O_2 \rightarrow C_2H_4+2H_2O$) is exothermic ($\Delta H$=−67 kcals/mole) and generally requires very high temperatures (>700° C.). As a consequence, the OCM reactors 102 can be sized, configured, and/or selected based upon the need to dissipate the heat generated by the OCM reaction, for example in some embodiments, multiple, tubular, fixed bed reactors can be arranged in parallel to facilitate heat removal. In at least some embodiments, at least a portion of the heat generated within the one or more OCM reactors 102 can be recovered, for example the heat can be used to generate high pressure steam. Where co-located with processes requiring a heat input, at least a portion of the heat generated within the one or more OCM reactors 102 may be transferred, for example using a heat transfer fluid, to the co-located processes. Where no additional use exists for the heat generated within the one or more OCM reactors 102, the heat can be released to the atmosphere, for example using a cooling tower or similar evaporative cooling device.

In other embodiments, the one or more OCM reactors 102 may include multiple adiabatic, fixed-bed, OCM reactors arranged in a cascaded series, where the OCM product gas generated by a first OCM reactor is removed and introduced to a second OCM reactor, subsequent cascaded OCM reactors can be similarly arranged. In at least some embodiments, the OCM product gas removed from each reactor may be cooled, for example in a horizontal or vertical tube boiler using boiler feed water to generate high pressure steam, prior to introduction to a subsequent OCM reactor. A multi-stage, cascaded OCM reactor arrangement advantageously provides the ability to control the thermal profile through each OCM reactor and through the entire cascaded OCM reactor series. The ability to provide independent reactor thermal profiling as well as thermal profiling throughout all of the cascaded reactors can improve catalyst performance and catalyst life as well as providing a degree of product selectivity in the OCM product gas 114.

In addition to a parallel configuration, multiple OCM reactors 102 may be arranged in a serial configuration or even a combination of series and parallel configurations. In a multiple reactor configuration, the OCM reactors 102 can be similar or different in size, type, or design based at least in part on process conversion and heat transfer specifications.

Chemical conversion is a measure of the quantity of reactants converted via a chemical reaction. Chemical selectivity is a measure of the quantity of a reactant converted to the desired product. For example, within the one or more OCM reactors, in addition to the desired ethylene, methane in the feedstock gas 112 will also be converted to undesirable or unwanted byproducts including, but not limited to, water vapor, oxides of carbon, and hydrogen. The ethylene selectivity of the one or more OCM reactors 102 is therefore a quantitative measure of their ability to convert methane in the feedstock gas 112 to ethylene in the OCM product gas 114. Conversion and selectivity are dependent upon a multitude of factors, including but not limited to: reactor design, catalyst, and operating conditions.

Although other OCM catalysts can be disposed in at least a portion of the one or more OCM reactors 102, in at least some embodiments, at least a portion of the OCM catalyst in at least a portion of the one or more OCM reactors can include one or more nanowire-based OCM catalysts such as those developed by Siluria Technologies Inc. (Palo Alto, Calif.) and described in: U.S. patent application Ser. No. 13/115,082, filed May 24, 2011, entitled "Nanowire Catalysts;" U.S. Provisional Patent Application Ser. 61/564,832, filed Nov. 29, 2011, entitled "Catalysts for Petrochemical Catalysis;" U.S. Provisional Patent Application Ser. 61/564,834, filed Nov. 29, 2011, entitled "Nanowire Catalysts;" and U.S. Provisional Patent Application Ser. 61/564,836, filed Nov. 29, 2011, entitled "Polymer Templated Nanowire Catalysts", all of which are incorporated in their entirety by reference as if reproduced in their entirety herein. Using one or more nanowire based OCM catalysts within the one or more OCM reactors 102, the selectivity of the catalyst in converting methane to desirable $C_2$ products can be about 10% or greater; about 20% or greater; about 30% or greater; about 40% or greater; about 50% or greater; about 60% or greater; about 65% or greater; about 70% or greater; about 75% or greater; about 80% or greater; or about 90% or greater.

The one or more OCM reactors 102 provide an OCM product gas 114. Although variable based upon a multitude of process equipment, reactant and process conditions, the OCM product gas 114 can contain in addition to the desired and valued ethylene product: water vapor, methane, ethane, nitrogen, hydrogen, carbon oxides, small quantities of heavier hydrocarbons (hydrocarbons containing three or more carbon atoms), acetylene or inert compounds. In exemplary embodiments, the ethylene content of the OCM product gas 114 can be about 0.5 mol % or greater; about 1 mol % or greater; about 2 mol % or greater; about 5 mol % or greater; about or more preferably about 7 mol % or greater and the ethane content of the OCM product gas 114 can be about 0.5 mol % or greater; about 1 mol % or greater; about 2 mol % or greater; about 5 mol % or greater; or more preferably about 7 mol % or greater. In at least some implementations, one or more inert gases, such as nitrogen, argon, or helium may be present in trace or larger quantities in the OCM product gas 114.

Considerable quantities of nitrogen can be present in the OCM product gas 114, particularly where air is used to supply all or a portion of the oxygen containing gas 106. Nitrogen is carried through the one or more OCM reactors 102 as an inert compound and may therefore appear at a relatively high concentration in the OCM product gas 114. In contrast, the nitrogen content of the OCM product gas 114 can be relatively low when purified oxygen, for example oxygen supplied by an air separation unit, is used to provide nearly all or all of the oxygen containing gas 106. In exemplary embodiments, the nitrogen content of the OCM product gas 114 can be about 1 mol % or less; about 5 mol % or less; about 10 mol % or less; about 25 mol % or less; about 40 mol % or less; or about 60 mol % or less. As discussed more fully below, the nitrogen or similar chemically inert gases in the OCM product gas 114 can be used advantageously in the separation unit 104 to provide some or all of the cooling required to recover $C_2$ compounds from the OCM product gas 114.

Hydrogen is liberated from the unsaturated hydrocarbons formed in the OCM reaction and may be present as a potential byproduct in the OCM product gas 114. The hydrogen content of the OCM product gas 114 can be about 4 mol % or less; about 3 mol % or less; about 2 mol % or less; or more preferably about 1 mol % or less.

Carbon oxides, including carbon monoxide and carbon dioxide, form as a result of the complete combustion of a portion of the hydrocarbons within the feedstock gas 112. Such combustion is an unintentional consequence of operating a high temperature hydrocarbon conversion process. In exemplary embodiments, the carbon oxide content of the OCM product gas 114 can be about 10 mol % or less; about 7 mol % or less; or more preferably about 5 mol % or less.

Within the one or more OCM reactors 102, the conversion of methane to heavier hydrocarbons is less than 100%. As a consequence, unreacted methane will be present in the OCM product gas 114. The quantity of methane within the OCM product gas will vary dependent upon the degree of conversion achieved within the one or more OCM reactors 102. In exemplary embodiments, the methane content of the OCM product gas 114 can be about 95 mole percent (mol %) or less; about 90 mol % or less; about 80 mol % or less; about 70 mol % or less; about 60 mol % or less; about 40 mol % or less; about 30 mol % or less; about 20 mol % or less; or about 10 mol % or less.

Where air is used to provide at least a portion of the oxygen containing gas 106, argon will accumulate due to the recycle of at least a portion of the non-condensable gas (principally nitrogen) from the separation unit 104 to the OCM reactors 102. In at least some situations, the argon content of the OCM product gas 110 can be 0 mol % for pure oxygen feed, about 1 mol % or less; about 5 mol % or less.

The temperature and pressure of the OCM product gas 114 is dependent upon maintaining a temperature and pressure profile within the one or more OCM reactors 102 that favors ethylene production while disfavoring the production of less desirable or undesirable by-products. Upon exiting the one or more OCM reactors 102, the OCM product gas 114 can be at a pressure of about 200 psig (1380 kPa) or less; about 150 psig (1035 kPa) or less; about 100 psig (690 kPa) or less; or more preferably about 50 psig (345 kPa) or less. Due to the exothermic nature of the OCM reaction, postcooling, for example by passing the OCM product gas 114 across a boiler feedwater preheater proximate the one or more OCM reactors 102. In exemplary embodiments, upon exiting the one or more OCM reactors 102, the OCM product gas 114 can be at a temperature of about 1750° F. (950° C.) or less; about 1650° F. (900° C.) or less; about 1560° F. (850° C.) or less; about 1470° F. (800° C.) or less; about 1380° F. (750° C.) or less; about 1300° F. (700° C.) or less; about 1100° F. (590° C.) or less; about 900° F. (480° C.) or less; about 700° F. (370° C.) or less; or about 500° F. (260° C.) or less.

Upon exiting the one or more OCM reactors 102, the OCM product gas 114 is at a relatively high temperature and a relatively low pressure. Recalling that the presence of one or more inert gasses (e.g., nitrogen) within the OCM product gas 114 can be used advantageously to reduce the temperature within the separation unit 104, the pressure of the OCM product gas 114 may also be increased using the one or more compressors 116 to provide a compressed OCM product gas 118. The temperature of the OCM product gas 114 may be adjusted using one or more pre-coolers (not shown) prior to introducing the OCM product gas 114 to the one or more compressors 116. The temperature of the compressed OCM product gas 118 may be reduced using one or more inter- or after-coolers after introducing the OCM product gas 114 to the one or more compressors 116. After exiting the one or more compressors 116, in exemplary embodiments the temperature of the compressed OCM product gas 118 can be about 150° F. (65° C.) or less; about 125° F. (52° C.) or less; about 100° F. (38° C.) or less; or about 75° F. (24° C.) or less. After exiting the one or more compressors 116, in exemplary embodiments the pressure of the compressed OCM product gas 118 can be at least about 100 psig (690 kPa); at least about 150 psig (1035 kPa); at least about 200 psig (1380 kPa); at least about 250 psig (1725 kPa); or at least about 300 psig (2070 kPa).

The compressed OCM product gas 118 may be introduced to the separation unit 104. Within the separation unit 104, the mixed gasses within the compressed OCM product gas 118 are separated to provide the methane rich effluent 120, the nitrogen rich effluent 122, and the $C_2$-rich effluent 124. In at least some embodiments, the separation unit can use in whole or in part, a cryogenic separation process to provide the methane rich effluent 120, the nitrogen rich effluent 122, and the $C_2$-rich effluent 124.

Acetylene may be present in the OCM product gas at concentrations of up to about 0.1 mole percent (mol %); about 0.2 mol %; about 0.3 mol %; about 0.4 mol %; about 0.5 mol %; or about 0.75 mol %. All or a portion of any acetylene present in the OCM product gas 114 may be removed from the OCM product gas 114. In at least some instances, at least a portion of any acetylene present in the OCM product gas 114 may be converted to at least one more preferable chemical species. For example, at least a portion of any acetylene present in the OCM product gas 114 may be converted to ethylene by passing all or a portion of the OCM product gas 114 through an acetylene reactor where the acetylene is catalytically, selectively, hydrogenated. In another implementation, at least a portion of any acetylene present may be fully hydrogenated to provide ethane. In yet another implementation, at least a portion of any acetylene present may be removed from the OCM product gas 114 and destroyed, for example via thermal combustion or oxidation in a controlled environment or via flare.

The gases in at least a portion of the compressed OCM product gas 118 may be adiabatically expanded to provide at least a portion of the cooling used in the cryogenic processes within the separation unit 104. In some embodiments, at least a portion of the gasses within the separation unit 104 may be recompressed and re-adiabatically expanded to provide additional cooling and, potentially, obviate the need for external refrigeration within the separation unit 104. Additionally, in some instances, at least a portion of the gasses within the separation unit 104 may be isentropically expanded, for example using a turboexpander, to provide mechanical work (e.g., a shaft output) useful within the separation unit 104.

Within the separation unit 104, heavier hydrocarbon compounds, including ethane and ethylene are separated from the OCM product gas 118 to provide the $C_2$-rich effluent 124 and a mixed nitrogen/methane containing gas. In some implementations, any acetylene present in the OCM product gas 118 may be at least partially removed using one or more systems, devices, or processes included in the separation unit 104. In other implementations, any acetylene present in the OCM Product gas 118 may be at least partially converted to one or more preferable chemical species using one or more systems, devices, or processes included in the separation unit 104. For example, all or a portion of the OCM product gas 118 or the $C_2$-rich effluent 124 may be passed through an acetylene reactor where at least a portion of the acetylene present in the OCM product gas 118 or the $C_2$-rich effluent 124 is selectively, catalytically hydrogenated to ethylene. Such acetylene removal or conversion may occur at any point in the separation unit 104, including preparatory to performing any separations (e.g., removal from the OCM product gas 118), after completion of the separations (e.g., removal from the $C_2$-rich effluent 124), at an intermediate stage of the separations process, or any combination thereof.

The mixed nitrogen/methane containing gas can be separated in separation unit to provide the nitrogen-rich effluent 122 and the methane-rich effluent 120. At least a portion of the methane-rich effluent 120 can be recycled back to the feedstock gas 112 or to the one or more OCM reactors 102. The methane-rich effluent 120 consists primarily of methane with other compounds present in small quantities. In exemplary embodiments, the methane content of the methane-rich effluent 120 can be about 60 mole percent (mol %) or greater; 80 mol % or greater; about 85 mol % or greater; about 90 mol % or greater; or more preferably about 95 mol % or greater. As explained above, the quantity and the concentration of nitrogen in the nitrogen-rich effluent 122 can depend upon the source used to supply the oxygen containing gas 106. In exemplary embodiments, the nitrogen content of the nitrogen-rich effluent 122 can be about 50 mol % or greater; about 75 mol % or greater; about 85 mol % or greater; or more preferably about 90 mol % or greater. The $C_2$-rich effluent 124 contains ethane, ethylene, and higher molecular weight hydrocarbons. In exemplary embodiments, the ethane content of the $C_2$-rich effluent 124 can be about 10 mol % or greater; about 20 mol % or greater; about 30 mol % or greater; about 40 mol % or greater; about 50 mol % or greater; or more preferably about 60% or greater and the ethylene content of the $C_2$-rich effluent 124 can be about 10 mol % or greater; about 20 mol % or greater; about 30 mol % or greater; about 40 mol % or greater; about 50 mol % or greater; or more preferably about 60 mol % or greater.

Figure 2:
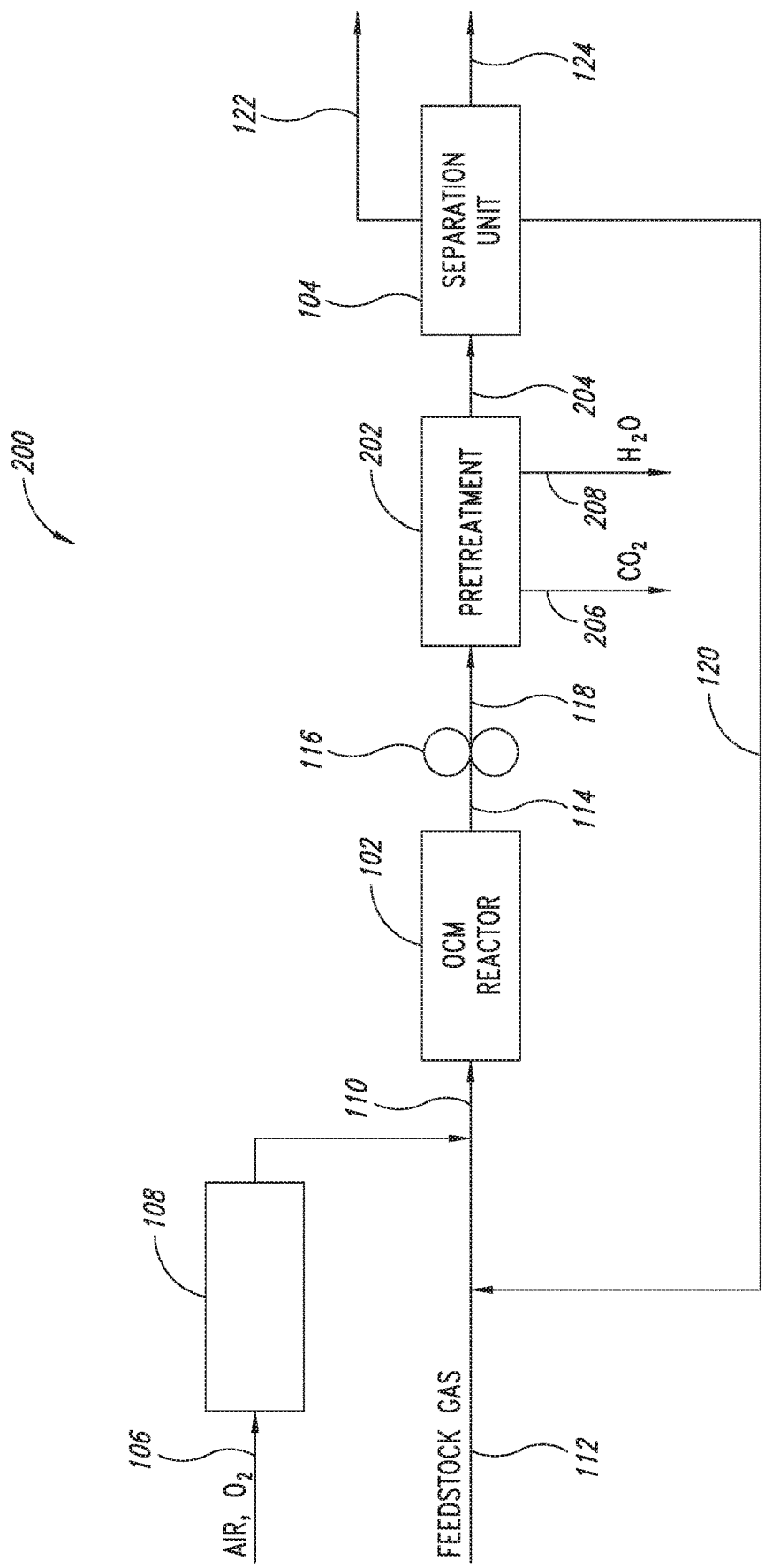
FIG. 2 is a block flow diagram depicting a methane based $C_2$ production, treatment, and separation process, according to one illustrated embodiment.

FIG. 2 is a block flow diagram depicting an illustrative $C_2$ production and separation process 200 having one or more oxidative coupling of methane (OCM) reactors 102, one or more separation units 104, and one or more pretreatment units 202. The one or more pretreatment units 202 are useful in removing contaminants and other undesirable compounds from the compressed OCM product gas 118 to provide a cleaned, compressed, OCM product gas 204. For example, water and carbon dioxide, both of which can freeze during a cryogenic process within the one or more separation units 104 may be removed from the compressed OCM product gas 118 in one or more pretreatment units 202. Although depicted as a single entity in FIG. 2, the one or more pretreatment units 202 can include multiple unit operations each targeting the reduction of the amount of one or more contaminants present within the compressed OCM product gas 118.

The compressed OCM product gas 118 can be introduced to the one or more pretreatment units 202 to remove one or more undesired components present in the compressed OCM product gas 118. For example, all or a portion of the carbon dioxide present within the compressed OCM product gas 118 can be removed within the one or more pretreatment units 202. Numerous methods of reducing the amount of carbon dioxide within the compressed OCM product gas 118 may be used. For example, the carbon dioxide level within the compressed OCM product gas 118 may be reduced by contacting the compressed OCM product gas 118 with a solution containing one or more amines such as monoethanolamine (MEA). In at least some embodiments at least a portion of the steam produced as a byproduct from the one or more OCM reactors can be used to facilitate the removal of carbon dioxide 206 from the compressed OCM gas 118 to provide the cleaned, compressed OCM product gas 204. For example, byproduct steam may be useful in the thermal regeneration of caustic that has been converted to calcium carbonate in a carbon dioxide scrubber. In exemplary embodiments, the carbon dioxide content of the cleaned, compressed OCM product gas 204 can be about 20 ppm or less; about 10 ppm or less; or more preferably about 5 ppm or less.

Additionally, all or a portion of the water 208 present in the compressed OCM gas 118 as a water vapor can be removed within the one or more pretreatment units 202. Numerous methods of reducing water vapor levels within the compressed OCM product gas 118 may be used. For example, the amount of water in the form of water vapor within the compressed OCM product gas 118 may be reduced using a thermal swing adsorption (TSA) process such as a multi-column TSA process enabling continuous water vapor removal and adsorbent bed regeneration. In at least some embodiments at least a portion of the steam produced as a byproduct from the one or more OCM reactors can be used to facilitate the regeneration of the adsorbent beds within a TSA process. In exemplary embodiments, the water vapor content of the cleaned, compressed OCM product gas 204 can be about 0.05 mol % or less; about 0.01 mol % or less; or more preferably about 0.001 mol % or less.

In at least some implementations, the pretreatment unit 202 may include one or more systems, devices, or processes to optionally remove at least a portion of any acetylene present in the OCM product gas 118. In other implementations, the pretreatment unit 202 may include one or more systems, devices, or processes to optionally convert at least a portion of any acetylene present in the OCM product gas 118 to one or more preferred chemical species. For example, in at least some implementations, all or a portion of the OCM product gas 118 may be passed through an acetylene reactor where at least a portion of the acetylene present in the OCM product gas 118 can be selectively, catalytically hydrogenated to ethylene.

Figure 3:
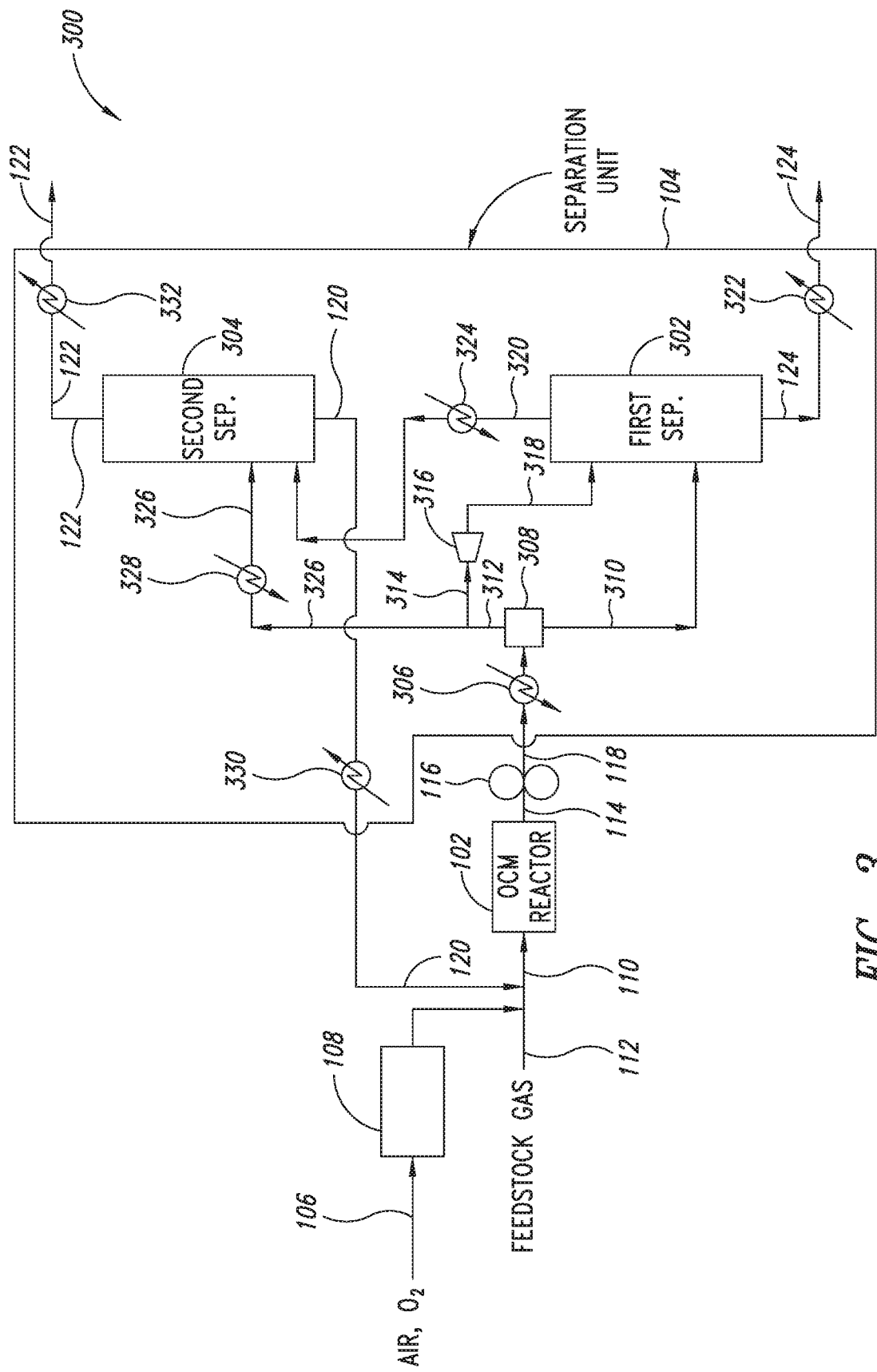
FIG. 3 is a basic process flow diagram depicting a methane based $C_2$ production and separation process, according to one illustrated embodiment.

FIG. 3 is a basic process flow diagram depicting a methane based $C_2$ production and separation process 300 including a first separator 302 providing the $C_2$-rich effluent 124 and a methane/nitrogen gas and a second separator 304 providing the methane-rich effluent 124 and the nitrogen-rich effluent 122. In the embodiment illustrated in FIG. 3, the temperature of the compressed OCM product gas 118 is reduced using one or more heat exchangers 306. The temperature of the compressed OCM product gas 118 may be lowered through the use of an external cooling media, a relatively cool process stream, or combinations thereof. Reducing the temperature of the OCM product gas 118 will condense at least a portion of the higher boiling point components in the compressed OCM product gas 118, including at least a portion of the $C_2$ and heavier hydrocarbons present in the compressed OCM product gas 118.

At least a portion of the condensed high boiling point components can be separated from the compressed OCM product gas 118 using one or more liquid/gas separators, such as knockout drums 308 to provide an OCM product gas condensate 310 and a compressed OCM product gas 312. The OCM product gas condensate 310 is introduced to the first separator 302 and at least a portion 314 of the compressed OCM product gas 312 can be introduced to one or more turboexpanders 316. The isentropic expansion of the compressed OCM product gas 314 within turboexpanders 316 can produce shaft work useful for driving one or more compressors or other devices in the separation unit 104. The isentropic expansion of the compressed OCM product gas 314 with the turboexpanders reduces the temperature of the compressed OCM product gas 318 that exits from the one or more turboexpanders. The compressed OCM product gas 318 from the one or more turboexpanders 316 is introduced to the first separator 302.

The first separator 302 can be any system, device or combination of systems and devices suitable for promoting the separation of $C_2$ and heavier hydrocarbons from a gas stream comprising mainly nitrogen and methane. For example, cryogenic distillation at a relatively high temperature may be used to promote the separation of $C_2$ and heavier hydrocarbons from a gas comprising mainly nitrogen and methane. The $C_2$-rich effluent 124 is withdrawn from the first separator 302 and a mixed nitrogen/methane containing gas mixture 320 is also withdrawn from the first separator 302. The nitrogen content of the nitrogen/methane containing gas mixture 320 withdrawn from the first separator 302 can be about 95 mol % or less; about 85 mol % or less; about 75 mol % or less; about 55 mol % or less; about 30 mol % or less. The balance of the nitrogen/methane gas mixture 320 comprises principally methane with small quantities of hydrogen, carbon monoxide, and inert gases such as argon.

In at least some embodiments, the first separator 302 may be referred to as a "demethanizer" based on its ability to separate methane from $C_2$ and higher hydrocarbons. An exemplary first separator 302 is provided by a vertical distillation column operating at below ambient temperature and above ambient pressure. The operating temperature and pressure within the first separator 302 can be established to improve the recovery of the desired $C_2$ hydrocarbons in the $C_2$-rich effluent 124. In exemplary embodiments, the first separator 302 can have an overhead operating temperature of from about −260° F. (−162° C.) to about −180° F. (−118° C.); about −250° F. (−157° C.) to about −190° F. (−123° C.); about −240° F. (−151° C.) to about −200° F. (−129° C.); or more preferably from about −235° F. (−148° C.) to about −210° F. (−134° C.) and an bottom operating temperature of from about −150° F. (−101° C.) to about −50° F. (−46° C.); about −135° F. (−93° C.) to about −60° F. (−51° C.); from about −115° F. (−82° C.) to about −70° F. (−57° C.); or more preferably about −100° F. (−73° C.) to about −80° F. (−62° C.). In exemplary embodiments, the first separator 302 can be at an operating pressure of from about 30 psig (205 kPa) to about 130 psig (900 kPa); about 40 psig (275 kPa) to about 115 psig (790 kPa); about 50 psig (345 kPa) to about 95 psig (655 kPa); or more preferably about 60 psig (415 kPa) to about 80 psig (550 kPa).

The temperature of at least a portion of the $C_2$-rich effluent 124 from first separator 302 can be increased in one or more heat exchangers 322 using a heat transfer fluid, a warm process flow stream, or a combination thereof. The one or more heat exchangers 322 can include any type of heat exchange device or system including, but not limited to one or more plate and frame, shell and tube, or the like. After exiting the one or more heat exchangers 322, in exemplary embodiments, the temperature of the $C_2$-rich effluent 124 can be about 50° F. (10° C.) or less; about 25° F. (−4° C.) or less; about 0° F. (−18° C.) or less; about −25° F. (−32° C.) or less; or about −50° F. (−46° F.) or less and the pressure can be about 130 psig (900 kPa) or less; about 115 psig (790 kPa) or less; about 100 psig (690 kPa) or less; or more preferably about 80 psig (550 kPa) or less.

The temperature of the nitrogen/methane containing gas mixture 320 withdrawn from the first separator 302 can be lowered in one or more heat exchangers 324 using one or more refrigerants, one or more relatively cool process flows, or combinations thereof. The one or more heat exchangers 324 can include any type of heat exchange device or system including, but not limited to one or more plate and frame, shell and tube, or the like. The cooled nitrogen/methane gas mixture 320 exiting one or more heat exchangers 324 is introduced to the second separator 304.

In some embodiments a portion 326 of the OCM product gas 312 removed from the knockout drum 308 and not introduced to the one or more turboexpanders 316 can be cooled using one or more heat exchangers 328. The one or more heat exchangers 328 can include any type of heat exchange device or system including, but not limited to one or more plate and frame, shell and tube, or the like. The temperature of the portion 326 of the OCM product gas 312 can be decreased using one or more refrigerants, one or more relatively cool process flows, or combinations thereof. The cooled portion 326 of the OCM product gas 312, containing a mixture of nitrogen and methane is introduced to the second separator 304.

The second separator 304 can be any system, device or combination of systems and devices suitable for promoting the separation of methane from nitrogen. For example, cryogenic distillation at a relatively low temperature can be used to promote the separation of methane from nitrogen in a gas stream. Conditions within the second separator 304 promote the condensation of methane and the separation of liquid methane from the gaseous nitrogen within the second separator 304. The liquid methane containing methane-rich effluent 120 is withdrawn as a liquid from the second separator 304 and the nitrogen-rich effluent 122 is withdrawn as a gas from the second separator 304. An exemplary second separator 304 is provided by a vertical distillation column operating significantly below ambient temperature and above ambient pressure. The operating temperature and pressure within the second separator 302 can be established to improve the separation of liquid methane as the methane-rich effluent 120 from the gaseous nitrogen as the nitrogen-rich effluent 122. For example, the second separator 304 can have an overhead operating temperature of from about −340° F. (−210° C.) to about −240° F. (−151° C.); about −330° F. (−201° C.) to about −250° F. (−157° C.); about −320° F. (−196° C.) to about −260° F. (162° C.); about −310° F. (−190° C.) to about −270° F. (−168° C.); or more preferably about −300° F. (−184° C.) to about −280° F. (−173° C.) and a bottom operating temperature of from about −280° F. (−173° C.) to about −170° F. (−112° C.); about −270° F. (−168° C.) to about −180° F. (−118° C.); about −260° F. (−162° C.) to about −190° F. (−123° C.); about −250° F. (−159° C.) to about −200° F. (−129° C.); or more preferably about −240° F. (−151° C.) to about −210° F. (−134° C.). In exemplary embodiments, the second separator 304 can be at an operating pressure of from about 85 psig (585 kPa) or less; about 70 psig (480 kPa) or less; about 55 psig (380 kPa) or less; or more preferably about 40 psig (275 kPa) or less.

The temperature of at least a portion of the methane-rich effluent 120 from the second separator 304 can be increased using one or more heat exchangers 330. In at least some instances, one or more compressors may be used to increase the pressure and temperature of the methane-rich effluent 120 from the second separator 304 prior to recycling at least a portion of the compressed methane-rich effluent 304 to the feedstock gas/oxygen containing gas mixture 110. The one or more heat exchangers 330 can include any type of heat exchange device or system including, but not limited to one or more plate and frame, shell and tube, or the like. The temperature of the methane-rich effluent 120 may be increased in heat exchangers 330 using a heat transfer fluid, a warm process flow, or a combination thereof. After exiting the one or more heat exchangers 330, in exemplary embodiments the temperature of the methane-rich effluent 120 can be about 125° F. (52° C.) or less; about 100° F. (38° C.) or less; or more preferably about 90° F. (32° C.) or less and the pressure of the methane-rich effluent 120 can be about 150 psig (1035 kPa) or less; about 100 psig (690 kPa) or less; or more preferably about 50 psig (345 kPa) or less. In an embodiment in accordance with FIG. 3, at least a portion of the methane-rich effluent 120 can be recycled to the feedstock gas 112, the feedstock gas/oxygen containing mixture 110, the compressed oxygen containing gas, or to the one or more OCM reactors 102.

The temperature of at least a portion of the nitrogen-rich effluent 122 can be increased using one or more heat exchangers 332. The one or more heat exchangers 332 can include any type of heat exchange device or system including, but not limited to one or more plate and frame, shell and tube, or the like. The temperature of the nitrogen-rich effluent 122 may be increased in heat exchangers 332 using a heat transfer fluid, a warm process flow, or a combination thereof. After exiting the one or more heat exchangers 332, in exemplary embodiments, the temperature of the nitrogen-rich effluent 122 can be about 125° F. (52° C.) or less; about 100° F. (38° C.) or less; or more preferably about 90° F. (32° C.) or less and the pressure of the nitrogen-rich effluent 122 can be about 150 psig (1035 kPa) or less; about 100 psig (690 kPa) or less; or more preferably about 50 psig (345 kPa) or less.

Although described above for brevity and clarity as independent heat exchange devices, the one or more heat exchangers 306, 322, 324, 328, 330, and 332 may be integrated into one or more composite heat exchange devices permitting, where appropriate, heat exchange between process flows of differing temperatures.

Figure 4:
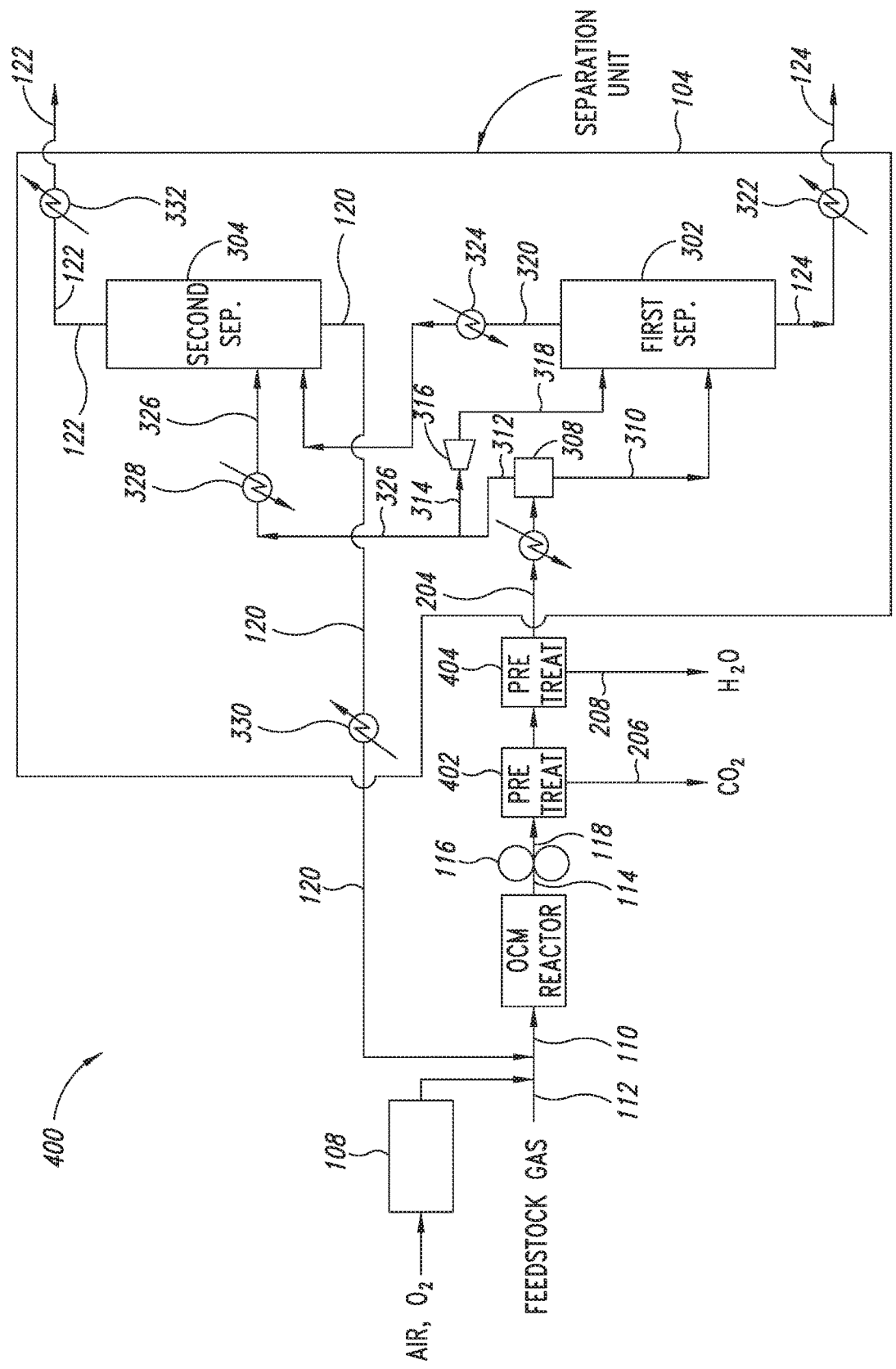
FIG. 4 is a basic process flow diagram depicting a methane based $C_2$ production, treatment and separation process, according to one illustrated embodiment.

FIG. 4 is a basic process flow diagram depicting a methane based $C_2$ production and separation process 400 including compressed OCM product gas 114 pretreatment, a first separator 302 providing the $C_2$-rich effluent 124 and a methane/nitrogen gas and a second separator 304 providing the methane-rich effluent 124 and the nitrogen-rich effluent 122. In some embodiments, the compressed OCM product gas 114 can be introduced to a carbon dioxide removal treatment system 402. Carbon dioxide removal treatment system can comprise systems suitable for removing carbon dioxide from OCM product gas 114. In some embodiments, an ethanolamine-based carbon dioxide removal process can be used to scrub carbon dioxide from the compressed OCM product gas 114. The spent ethanolamine solution can be regenerated via heating thereby providing a recyclable carbon dioxide scrubbing solution. In other embodiments, a caustic-based carbon dioxide removal process can be used to scrub carbon dioxide from the compressed OCM product gas 114. In some instances, the sodium carbonate formed by scrubbing the carbon dioxide from the compressed OCM product gas 114 can be reacted with calcium hydroxide to form calcium carbonate and regenerate the caustic for recycle to the carbon dioxide removal treatment system 402.

The compressed OCM product gas 114 can also be introduced to a water removal system 404 that includes systems for removing water from OCM product gas 114. In some embodiments, the water removal system can include a thermal swing adsorption (TSA) system having at least two TSA columns to provide continuous water removal capability. Further details of exemplary TSA water removal systems have been described above.

Figure 5:
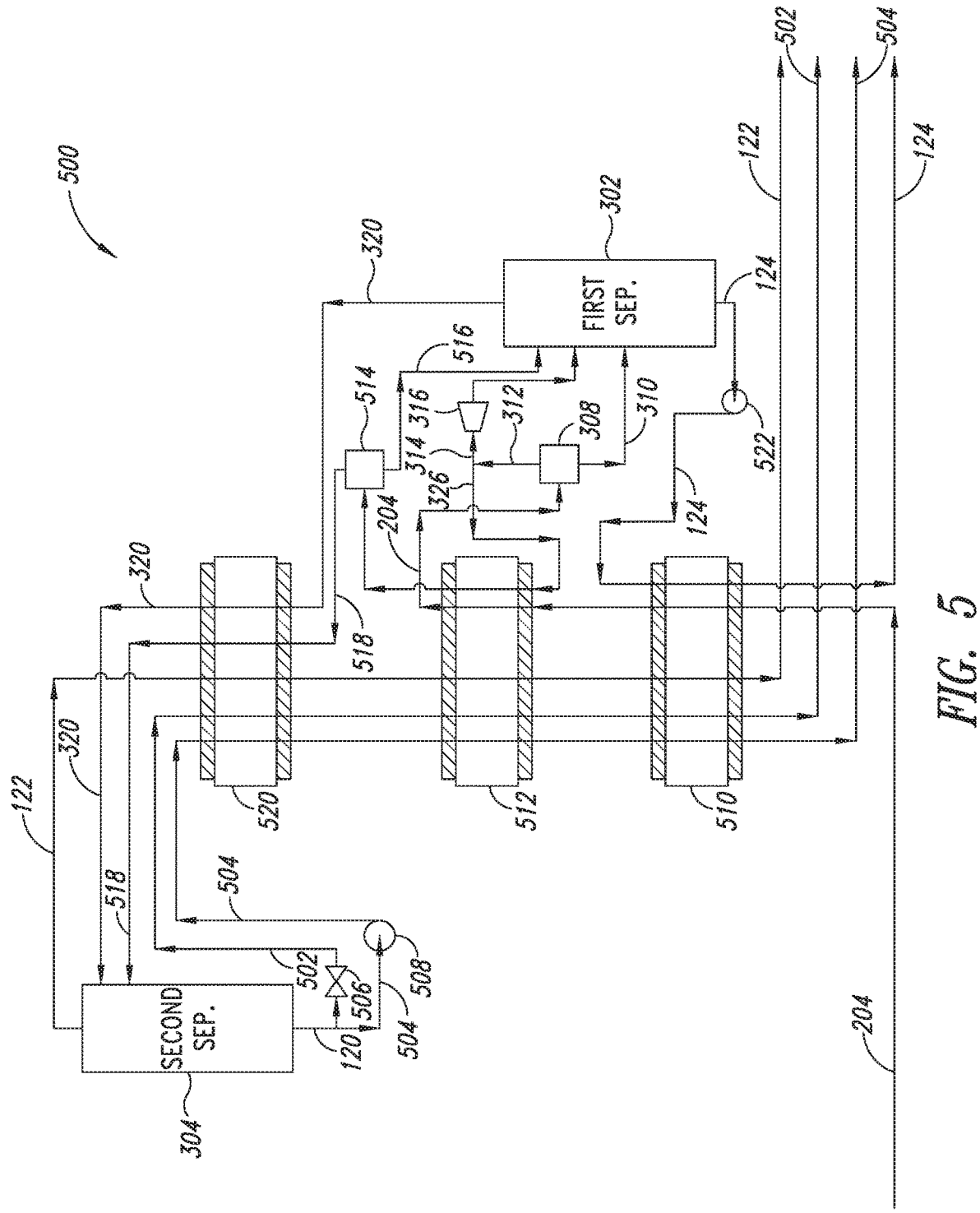
FIG. 5 is a process flow diagram depicting a separation process useful for separating a mixed product gas stream resulting from a methane based $C_2$ production process, according to one illustrated embodiment.

FIG. 5 is a process flow diagram depicting a separation process 500 useful within one or more separation units 104 to separate the cleaned, compressed OCM product gas 204, according to one illustrated embodiment. As depicted in FIG. 5, heat exchange between various process streams is used to provide process heating and cooling as needed. Importantly, the adiabatic expansion of one or more process gasses coupled with the use of process heat exchange can minimize or even eliminate the requirement for the supply of external refrigeration to the separation process 500. In some instances, for example where purified or separated oxygen provides at least a portion of the oxygen containing gas 106, insufficient gas volume within the separation unit 104 may serve to limit the cooling effect realized by the adiabatic expansion of process gas within the separation unit 104. In such embodiments, external cooling, for example cooling from a cryogenic process providing the oxygen containing gas 106 may be used to provide at least a portion of the cooling within the separation unit 104.

In at least some embodiments, the pressure of the methane-rich effluent 120 withdrawn from the second separator 304 may be adjusted to provide a methane-rich effluent at two or more pressures. Such an arrangement may be advantageous for example, when a first portion 502 of the methane-rich effluent 120 is intended for distribution within a commercial or industrial distribution network operating at a relatively low pressure and a second portion 504 of the methane-rich effluent 120 is intended for injection into a transport pipeline operating at a relatively high pressure. For example, the pressure of the first portion 502 of the methane-rich effluent 120 may be reduced to a pressure of from about 5 psig (35 kPa) to about 30 psig (205 kPa) by passing portion 502 of the methane-rich effluent 120 through a pressure reduction device such as a pressure reducing valve 506. The pressure of the second portion 504 of the methane-rich effluent 120 may be increased to a pressure of from about 30 psig (205 kPa) to about 100 psig (690 kPa) by passing portion 504 of the methane-rich effluent 120 through a pressure increasing device such as a fluid mover 508.

The cleaned, compressed OCM product gas 204 is introduced to the separation process 500. Recall, the OCM product gas exiting the one or more OCM reactors 102 is at an elevated temperature. While the OCM product gas is cooled, the temperature of the OCM product gas entering the separation process 500 remains at a relatively warm temperature, for example between about 50° F. (10° C.) and 150° F. (66° C.). Conversely, the $C_2$-rich effluent 124 withdrawn from the first separator 302 is typically at a relatively cool temperature, for example between about −150° F. (−101° C.) and about −80° F. (−62° C.). The first and second portions 502, 504 of the methane-rich effluent 120 and the nitrogen-rich effluent 122 withdrawn from the second separator 304 are also typically at relatively cool temperatures, for example between −340° F. (−207° C.) and about −170° F. (−112° C.). By thermally contacting the relatively warm cleaned, compressed OCM product gas 204 with the relatively cool $C_2$-rich effluent 124, first and second portions 502, 504 of the methane-rich effluent 120 and the nitrogen-rich effluent 122 in a first heat exchange device 510, the temperature of the cleaned, compressed OCM product gas 204 can be decreased and the temperature of the effluent streams increased. The first heat exchange device 510 can be any type, size, or shape heat exchange device capable of transferring heat between three or more components.

Recall from FIG. 3 the OCM product gas 312 removed from the knockout drum 308 can be apportioned or otherwise separated into a first portion 314 that is introduced to the one or more turboexpanders 316 and a second portion 326 that is ultimately introduced to the second separator 304. The adiabatic expansion of the cleaned, compressed OCM product gas 204 within the knockout drum 308 reduces the temperature of the OCM product gas 312 exiting drum 308. Thus, the temperature of the second portion of the OCM product gas 326 will be at a lower temperature than the cleaned, compressed OCM product gas 204 entering knockout drum 308.

By thermally contacting the relatively warm cleaned, compressed OCM product gas 204 and the second portion of the OCM product gas 326 with the relatively cool first and second portions 502, 504 of the methane-rich effluent 120 and the nitrogen-rich effluent 122 in a second heat exchange device 512, the temperature of the cleaned, compressed OCM product gas 204 and the second portion of the OCM product gas 326 can be further decreased and the temperature of the effluent streams increased. The second heat exchange device 512 can be any type, size, or shape heat exchange device capable of transferring heat between three or more components.

Cooling the second portion of the OCM product gas 326 can form a second OCM product gas condensate within the second portion of the OCM product gas 326. The second portion of the OCM product gas 326 can be introduced to a liquid/gas separation device, such as a knockout drum 514 where the second OCM product gas condensate 516 is removed and returned to the first separator 302, for example as a reflux to the first separator 302. The OCM product gas 518 is withdrawn from the drum 514 and introduced to the second separator 304.

In some embodiments, by thermally contacting the relatively warm OCM product gas 518 and the nitrogen/methane gas mixture 320 withdrawn from the first separator 302 with the relatively cool first and second portions 502, 504 of the methane-rich effluent 120 and the nitrogen-rich effluent 122 from second separator 304 in a third heat exchange device 520, the temperature of the OCM product gas 518 and the nitrogen/methane gas mixture 320 can be further decreased and the temperature of the effluent streams increased. The third heat exchange device 512 can be any type, size, or shape heat exchange device capable of transferring heat between three or more components.

In at least some embodiments, the pressure of the $C_2$-rich effluent 124 withdrawn from the first separator 302 can be increased, for example through the use of one or more fluid movers 522. The $C_2$-rich effluent 124 contains a mixture of ethane, ethylene and heavier hydrocarbons such as propane, butane, pentane and hexane. In at least some embodiments, all or a portion of the $C_2$-rich effluent 124 can be fractionated or otherwise separated, for example within a $C_2$ separation process or column (e.g. a "de-ethanizer") to provide at least an ethylene-rich effluent and an ethane-rich effluent. The ethylene-rich effluent can provide either a feedstock to a subsequent process or a fungible product. All or a portion of the ethane may be recycled back to the feedstock gas 112.

Figure 6:
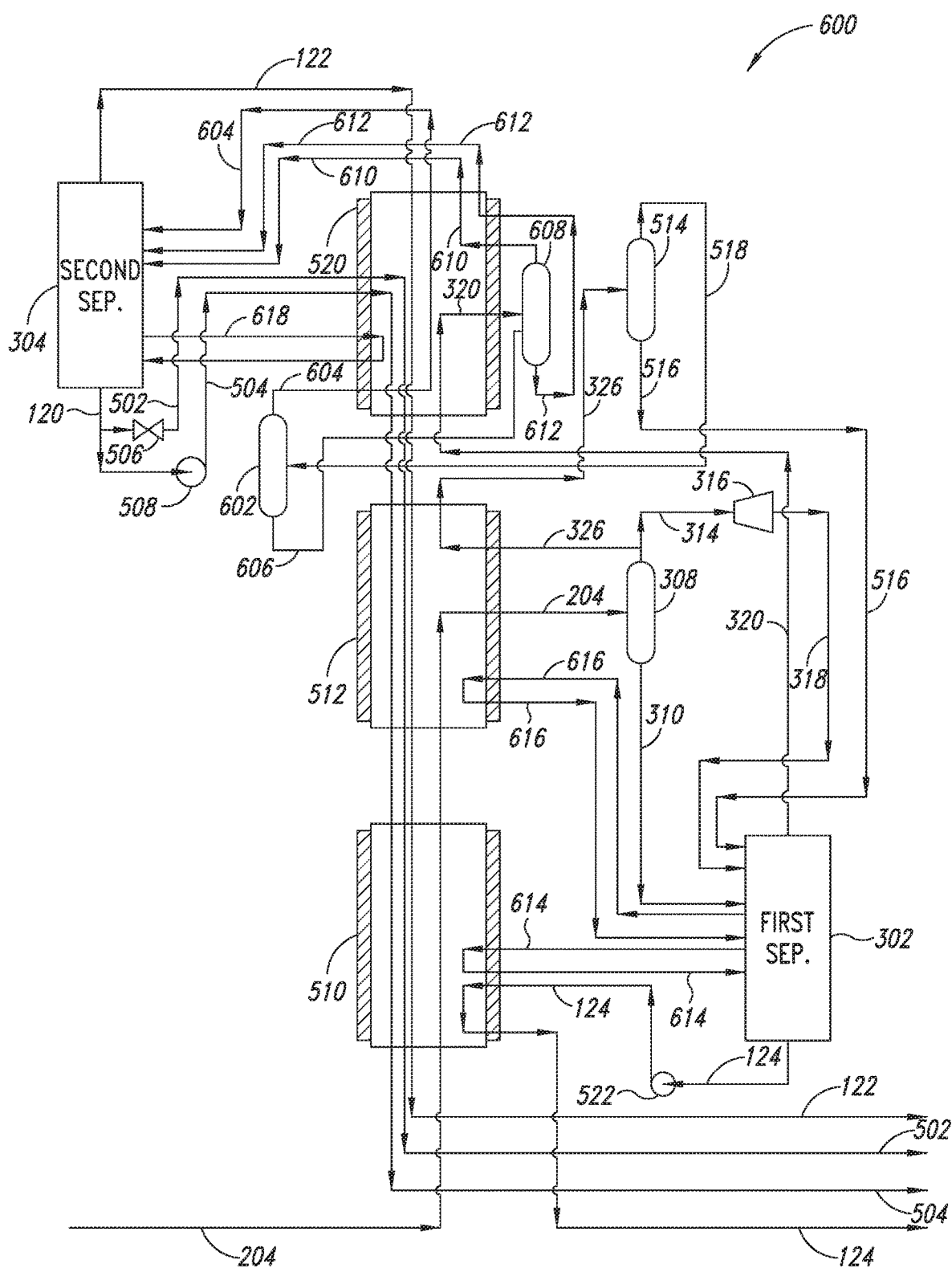
FIG. 6 is a process flow diagram depicting another separation process useful for separating a mixed product gas stream resulting from a methane based $C_2$ production process, according to one illustrated embodiment.

FIG. 6 is a process flow diagram depicting another separation process 600 within one or more separation units 104 to separate the cleaned, compressed OCM product gas 204 into desired fractions, according to one illustrated embodiment. As depicted in FIG. 6, in addition to heat exchange between various process streams to provide process heating and cooling as needed, heat exchange is also useful for providing one or more reboiler loops (i.e., thermal energy inputs) to the first separator 302 and the second separator 304. Additionally, the nitrogen/methane gas mixture 320 from the first separator 302 and the OCM product gas 518 from knockout drum 514 may also provide one or more thermal contributions to the third heat exchanger 520.

In at least some embodiments, the OCM product gas 518 withdrawn from the knockout drum 514 is introduced to a second knockout drum 602. Non-condensed OCM product gas 604 is withdrawn from the second knockout drum 602. The temperature of the OCM product gas 604 can be reduced in the third heat exchanger 520 prior to introducing the OCM product gas 604 to the second separator 304. Any OCM product gas condensate 606 in the second knockout drum 602 is withdrawn and introduced to a third knockout drum 608.

In at least some embodiments, the nitrogen/methane gas mixture 320 can be withdrawn from the first separator 302 and introduced to the third heat exchanger 520 where a portion of the nitrogen/methane gas mixture 320 can condense. Any condensate present in either or both the nitrogen/methane gas mixture 320 and the OCM product gas condensate 606 are separated in the third knockout drum 608. The gas 610 within the third knockout drum 608, comprising the nitrogen/methane gas mixture 320 and any OCM product gas from the OCM product gas condensate 606 are withdrawn from the third knockout drum 608. The temperature of the relatively warm gas 610 is increased using the third heat exchanger 520 prior to introducing the gas 610 to the second separator 304. Similarly, relatively warm condensate 612 from the third knockout drum 608 is withdrawn from the drum 608 and the temperature of the condensate 612 increased using the third heat exchanger 520 prior to introducing the condensate 612 to the second separator 304.

In some embodiments, the thermal efficiency of the separation unit 104 may be improved by the transfer of thermal energy (i.e. heat) from the first heat exchanger 510 and the second heat exchanger 512 to the first separator 302 via reboiler loops 614 and 616, respectively. Similarly, additional thermal efficiency may be realized by the transfer of thermal energy (i.e. heat) from the third heat exchanger 520 to the second separator 304 via reboiler loop 618. In some embodiments, the thermal energy may be transferred between the heat exchangers and the separators using a closed loop heat transfer fluid. In other embodiments, the liquid present in the separator may be withdrawn and passed through the respective heat exchanger. In yet other embodiments, a portion of the first and second heat exchangers 510, 512 may be partially or completely disposed within the first separator 302 and a portion of the third heat exchanger 520 may be partially or completely disposed within the second separator 304.

Figure 7:
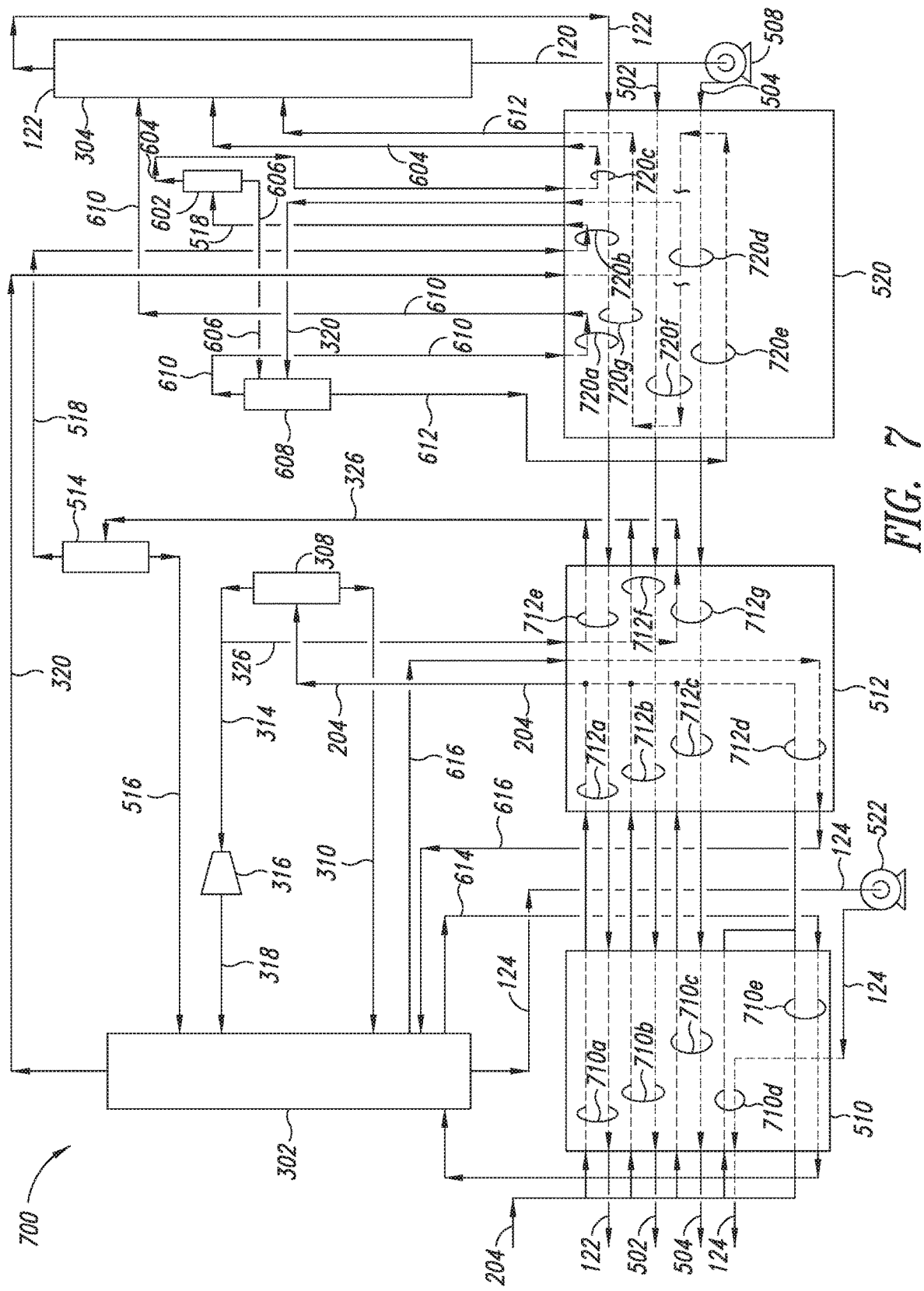
FIG. 7 is a process flow diagram depicting a detail heat exchanging scheme of another separation process useful for separating a mixed product gas stream resulting from a methane based $C_2$ production process, according to one illustrated embodiment.

The process flow diagram shown in FIG. 7 provides a more detailed breakdown of the thermal conservation process 700 that occurs in the first heat exchanger 510, the second heat exchanger 512, and the third heat exchanger 520, according to one implementation. The thermal transfer processes occurring in each of the first heat exchanger 510, the second heat exchanger 512, and the third heat exchanger 520 are described in greater detail in Tables 1, 2, and 3 that follow. In the following tables, the term "hot stream" refers to a gas, liquid, or combination thereof whose thermal energy or temperature decreases as the gas, liquid, or combination thereof passes through the heat exchanger. In the following tables, the term "cold stream" refers to a gas, liquid, or combination thereof whose thermal energy or temperature increases as the gas, liquid, or combination thereof passes through the heat exchanger. For convenience and ease of description, each of heat exchangers 510, 512, and 520 are broken into a number of thermal cells in the following tables. One of ordinary skill in the chemical engineering art would readily appreciate that such cells may be freely added, removed or changed between heat exchangers to provide alternate levels of thermal conservation provided by the thermal conservation process 700. Although only one cold stream and one hot stream are shown as included in each thermal cell, one of ordinary skill in the chemical engineering arts would readily appreciate that more than two streams (e.g., one hot stream and two cold streams, etc.) could be readily passed through a single thermal cell.

TABLE 1

HEAT EXCHANGER 510 THERMAL CELLS

| Cell ID | # | Cold Gas/Liquid | # | Hot Gas/Liquid |
|---|---|---|---|---|
| 710a | 122 | Nitrogen rich effluent | 204 | OCM product gas |
| 710b | 502 | 1$^{st}$ methane rich effluent | 204 | OCM product gas |
| 710c | 504 | 2$^{nd}$ methane rich effluent | 204 | OCM product gas |
| 710d | 124 | C$_2$-rich effluent | 204 | OCM product gas |
| 710e | 614 | 302 Reboiler loop | 204 | OCM product gas |

TABLE 2

HEAT EXCHANGER 512 THERMAL CELLS

| Cell ID | # | Cold Gas/Liquid | # | Hot Gas/Liquid |
|---|---|---|---|---|
| 712a | 122 | Nitrogen rich effluent | 204 | OCM product gas |
| 712b | 502 | 1$^{st}$ methane rich effluent | 204 | OCM product gas |
| 712c | 504 | 2$^{nd}$ methane rich effluent | 204 | OCM product gas |
| 712d | 616 | 302 Reboiler loop | 204 | OCM product gas |
| 712e | 122 | Nitrogen rich effluent | 326 | OCM product gas fraction |
| 712f | 502 | 1$^{st}$ methane rich effluent | 326 | OCM product gas fraction |
| 712g | 504 | 2$^{nd}$ methane rich effluent | 326 | OCM product gas fraction |

TABLE 3

HEAT EXCHANGER 520 THERMAL CELLS

| Cell ID | # | Cold Gas/Liquid | # | Hot Gas/Liquid |
|---|---|---|---|---|
| 720a | 122 | Nitrogen rich effluent | 610 | K/O drum gas |
| 720b | 122 | Nitrogen rich effluent | 518 | OCM product gas |
| 720c | 122 | Nitrogen rich effluent | 604 | Non-cond. OCM prod. gas |
| 720d | 504 | 2$^{nd}$ methane rich effluent | 320 | N$_2$/CH$_4$ gas mixture |
| 720e | 504 | 2$^{nd}$ methane rich effluent | 612 | Condensate |
| 720f | 502 | 1$^{st}$ methane rich effluent | 612 | Condensate |
| 720g | 122 | Nitrogen rich effluent | 612 | Condensate |

Figure 8:
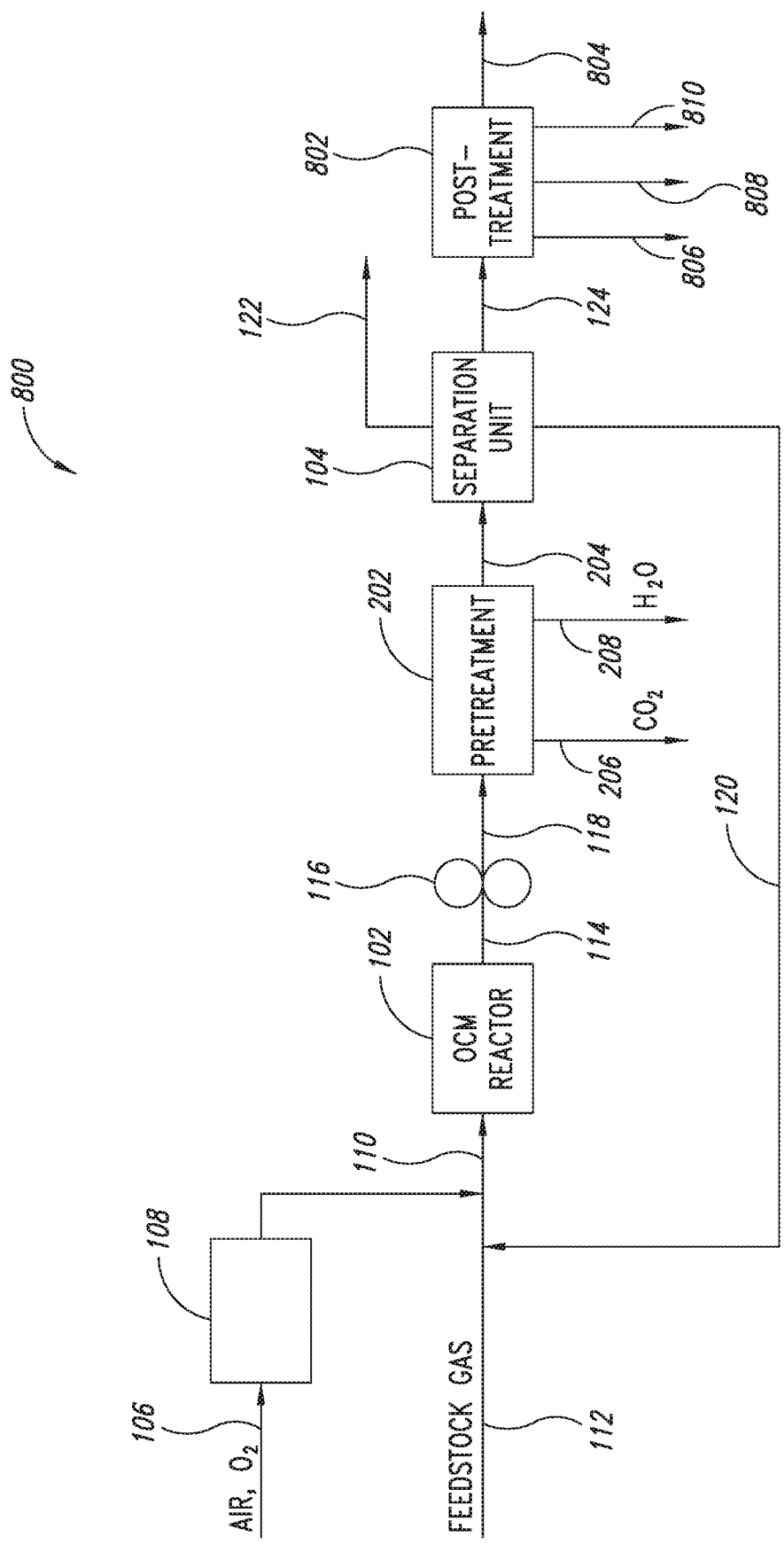
FIG. 8 is a block flow diagram depicting another methane based $C_2$ production and separation process, according to one illustrated embodiment.

The block flow diagram 800 depicted in FIG. 8 shows an optional post-treatment system 802 to which at least a portion of the C$_2$-rich effluent 124 is introduced. In at least some instances, the post-treatment system 802 may include any number of unit operations. For example, the post-treatment system 802 may include one or more devices, systems, or processes to provide an ethylene-rich effluent 804. Such an ethylene-rich effluent 804 may be useful in any number of subsequent processes, for example an oligomerization or catalytic polymerization process to produce a liquid gasoline product commonly referred to as polygas.

In at least some implementations, the post-treatment system 802 includes any number of systems, devices, or processes for reducing the quantity of any acetylene in the C$_2$-rich effluent 124. In at least some situations, such reduction may occur by removing as an acetylene-rich effluent 806 at least a portion of any acetylene present in the C$_2$-rich effluent 124. In at least some situations, such reduction may occur by converting at least a portion of any acetylene present in the C$_2$-rich effluent 124 to one or more preferred chemical species. In at least some implementations, the acetylene concentration in the C$_2$-rich effluent 124 can be reduced to less than about 1 part per million by volume (ppmv); less than about 3 ppmv; less than about 5 ppmv; or less than about 10 ppmv after removal or conversion in the post-treatment system 802.

In at least some instances, the C$_2$-rich effluent 124 may be further separated the post-treatment system 802. The C$_2$-rich effluent 124 may include a number of chemical species that includes a mixture of ethane, ethylene, and C$_{3+}$ hydrocarbons. In at least some implementations, the ethane, ethylene, and C$_{3+}$ hydrocarbons may be partially or wholly separated or otherwise isolated in the post-treatment system 802. The separation of the C$_2$-rich effluent 124 into a ethane, ethylene, and C$_{3+}$ can provide at least the ethylene-rich effluent 804, an ethane-rich effluent 808, and a C$_{3+}$-rich effluent 810. In at least some implementations, all or a portion of the C$_2$-rich effluent 124 may be introduced to one or more systems, devices, or processes in which ethylene may be segregated, removed or otherwise isolated to provide the ethylene-rich effluent 804. In at least some instances, the ethylene-rich effluent 804 may include the overhead product of a distillation or cryogenic distillation process, for example a distillation process including at least one distillation column that is colloquially known within the chemical arts as a "$C_2$ Splitter" that operates at a reduced temperature and an elevated pressure. In such instances, the ethylene-rich effluent 804 so produced may have an ethylene concentration of about 75 mole percent (mol %) or more; about 80 mol % or more; about 85 mol % or more; about 90 mol % or more; about 95 mol % or more; about 99 mol % or more; or about 99.9 mol % or more.

In at least some implementations, the mixture of ethane and $C_{3+}$ hydrocarbons remaining after the removal of at least a portion of the ethylene present in the $C_2$-rich effluent 124 may be introduced to one or more systems, devices, or processes in which all or a portion of the ethane may be segregated, removed or otherwise isolated to provide the ethane-rich effluent 808. In at least some instances, the ethane-rich effluent 808 may include at least a portion of the overhead product of a distillation or cryogenic distillation process, for example a distillation process that includes at least one distillation column operating at a reduced temperature and an elevated pressure. In such instances, the ethane-rich effluent 808 so produced may have an ethane concentration of about 75 mole percent (mol %) or more; about 80 mol % or more; about 85 mol % or more; about 90 mol % or more; about 95 mol % or more; about 99 mol % or more; or about 99.9 mol % or more. In such instances, the $C_{3+}$-rich effluent 810 may include at least a portion of the bottoms from the ethane separation process. In such instances, the $C_{3+}$-rich effluent 810 so produced may have a $C_{3+}$ hydrocarbon concentration of about 75 mole percent (mol %) or more; about 80 mol % or more; about 85 mol % or more; about 90 mol % or more; about 95 mol % or more; about 99 mol % or more; or about 99.9 mol % or more.

Prophetic Example

Referring to FIG. 2, the following prophetic example illustrates a compositional analysis of an exemplary OCM process in accordance with embodiments disclosed herein with separation of the $C_2$-rich effluent 124, the nitrogen-rich effluent 122 and the methane-rich effluent 120.

| Ref # | Flow (klb/hr) | $C_1$ Mol % | $N_2$ Mol % | $O_2$ Mol % | $H_2O$ Mol % | CO Mol % | $CO_2$ Mol % | $C_2$ Mol % | $C_2$= Mol % |
|---|---|---|---|---|---|---|---|---|---|
| 106 | 36.4 | 0 | 78 | 21 | 0 | 0 | 0 | 0 | 0 |
| 112 | 5.8 | 99 | 0 | 0 | 0 | 0 | 0 | 0 | 0 |
| 110 | 56.9 | 48 | 39 | 10 | 0 | 0 | 0 | 0 | 0 |
| 114 | 56.9 | 37 | 39 | 0 | 12 | 1.1 | 2.4 | 2 | 1.8 |
| 204 | 46.9 | 44 | 47 | 0 | 0 | 1.3 | 0 | 2.4 | 2.1 |
| 120 | 15.5 | 97 | 0.5 | 0 | 0 | 0.5 | 0 | 0 | 0 |
| 122 | 28.6 | 1 | 91 | 0 | 0 | 2.2 | 0 | 0 | 0 |
| 124 | 2.8 | 1 | 0 | 0 | 0 | 0 | 0 | 52 | 43 |

Although described in the context of an oxidative coupling of methane (OCM) process, the disclosed systems and methods can be applied to the separation of a similarly composed $C_2$-rich effluent 124 from processes similar to or different from the OCM production process described in detail herein. As an example, another process providing a gaseous effluent similar to the OCM product gas 114 is provided by an oxidative dehydrogenation of ethane to form ethylene using air as the oxygen comprising feed gas.

The invention claimed is:

1. A system for providing $C_2$ compounds via oxidative coupling of methane (OCM), comprising:
   at least one catalytic OCM reactor system including at least one OCM catalyst to provide an OCM product gas including at least ethane, ethylene, oxygen and nitrogen, wherein each OCM reactor system includes at least a means to provide a gas mixture including at least methane and oxygen prior to introduction to at least one OCM reactor;
   at least one OCM product gas compressor that receives the OCM product gas and generates a compressed OCM product gas having a pressure of 200 pounds per square inch gauge (psig) or more;
   a first liquid/gas separator that receives the compressed OCM product gas and generates a first OCM product gas stream and a first OCM product gas condensate;
   a turboexpander that receives a first portion of the first OCM product gas stream and generates an expanded first OCM product gas stream and a mechanical shaft work output;
   a second liquid/gas separator that receives a second portion of the first OCM product gas stream and generates a second OCM product gas stream and a second OCM product gas condensate;
   a first separations system that receives the first OCM product gas condensate, the expanded first OCM product gas stream, and the second OCM product gas condensate and performs a cryogenic separation to generate at least a $C_2$-rich effluent that includes at least one $C_2$ compound and a gas mixture effluent that includes methane and nitrogen;
   a second separations system that receives the second OCM product gas stream and the gas mixture effluent and performs a cryogenic separation to generate a methane-rich effluent and a nitrogen-rich effluent;
   a first heat exchanger that exchanges thermal energy from the compressed OCM product gas to the methane-rich effluent, the nitrogen-rich effluent, and the $C_2$-rich effluent;
   a second heat exchanger that exchanges thermal energy from the compressed OCM product gas and the second portion of the first OCM product gas stream to the methane-rich effluent and the nitrogen-rich effluent; and
   a third heat exchanger that exchanges thermal energy from the second OCM product gas stream and the gas mixture effluent to the methane-rich effluent and the nitrogen-rich effluent.

2. The system of claim 1, further comprising a preheater that heats a feedstock gas comprising methane to a temperature of about 600° C. or less, and wherein at least a portion of the methane in the gas mixture is provided by the feedstock gas.

3. The system of claim 1 further comprising:
at least one water removal system to reduce the water concentration in the compressed OCM product gas to about 0.001 mole percent (mol %) or less.

4. The system of claim 3 further comprising:
at least one carbon dioxide removal system to reduce the carbon dioxide concentration of the compressed OCM product gas to about 5 parts per million by volume (ppmv) or less.

5. The system of claim 1 further comprising:
at least one acetylene removal system to reduce the acetylene concentration of the compressed OCM product gas to about 1 part per million by volume (ppmv) or less.

6. The system of claim 1, further comprising:
at least one acetylene removal system to reduce the acetylene concentration of the $C_2$-rich effluent to about 1 part per million by volume (ppmv) or less.

7. The system of claim 1, further comprising:
a third separations unit to cryogenically separate at least a portion of the $C_2$-rich effluent into an ethylene-rich effluent having an ethylene concentration of about 90 mole percent (mol %) or more and an ethane-rich effluent having an ethylene concentration of about 1 mol % or less.

8. The system of claim 7, further comprising:
a fourth separations unit to cryogenically separate at least a portion of the ethane-rich effluent into an ethane-rich effluent having an ethane concentration of about 90 mole percent (mol %) or more and a $C_{3+}$-rich effluent having an ethane concentration of about 1 mol % or less.

9. The system of claim 1, further comprising:
at least one hydrogen sulfide removal system to reduce the hydrogen sulfide concentration of a feedstock gas comprising methane to about 5 parts per million by volume (ppmv) or less prior to the at least one OCM reactor system.

10. The system of claim 1, wherein the at least one OCM catalyst comprises at least one OCM nanowire catalyst.

* * * * *